United States Patent
Xu et al.

(10) Patent No.: US 8,987,167 B2
(45) Date of Patent: Mar. 24, 2015

(54) LOW VOLATILE AMINE SALTS OF ANIONIC PESTICIDES

(75) Inventors: Wen Xu, Cary, NC (US); Paul Ch. Kierkus, Wake Forest, NC (US); Steven Brunt, Raleigh, NC (US); Steven Bowe, Apex, NC (US); Adam Hixson, Raleigh, NC (US); Terrance M. Cannan, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/498,779

(22) PCT Filed: Sep. 28, 2010

(86) PCT No.: PCT/EP2010/064343
§ 371 (c)(1),
(2), (4) Date: Mar. 28, 2012

(87) PCT Pub. No.: WO2011/039172
PCT Pub. Date: Apr. 7, 2011

(65) Prior Publication Data
US 2012/0184434 A1    Jul. 19, 2012

Related U.S. Application Data

(60) Provisional application No. 61/247,005, filed on Sep. 30, 2009, provisional application No. 61/348,758, filed on May 27, 2010.

(30) Foreign Application Priority Data

Oct. 19, 2009 (EP) ...................................... 09173368

(51) Int. Cl.
*A01N 25/26* (2006.01)
*A01N 3/02* (2006.01)
*A01N 37/40* (2006.01)
*A01N 39/04* (2006.01)
*A01N 57/20* (2006.01)

(52) U.S. Cl.
CPC ................ *A01N 37/40* (2013.01); *A01N 39/04* (2013.01); *A01N 57/20* (2013.01)
USPC .......................................... 504/100; 504/113

(58) Field of Classification Search
None
See application file for complete search history.

(56) References Cited

U.S. PATENT DOCUMENTS

| | | | |
|---|---|---|---|
| 3,683,010 A * | 8/1972 | Reck et al. ..................... | 562/472 |
| 3,852,340 A | 12/1974 | Reck et al. | |
| 4,405,531 A | 9/1983 | Franz | |
| 5,035,738 A | 7/1991 | Burns et al. | |
| 5,175,353 A | 12/1992 | Jones et al. | |
| 5,221,791 A | 6/1993 | Narayanan et al. | |
| 6,133,199 A * | 10/2000 | Soula et al. ................... | 504/206 |
| 2004/0097372 A1 | 5/2004 | Abraham et al. | |
| 2010/0273654 A1 | 10/2010 | Li et al. | |

FOREIGN PATENT DOCUMENTS

| | | |
|---|---|---|
| CA | 936865 | 11/1973 |
| CA | 2008553 | 7/1990 |
| EP | 0 183 384 | 6/1986 |
| EP | 0 375 624 | 6/1990 |
| EP | 0 379 624 | 8/1990 |
| GB | 1 078 804 | 8/1967 |
| WO | WO 91/04661 | 4/1991 |
| WO | WO 97/24931 | 7/1997 |
| WO | WO 2009/068226 | 6/2009 |
| WO | WO 2012/059494 | 5/2012 |

OTHER PUBLICATIONS

Behrens, Richard, et al., "Dicamba Volatility", Weed Science, 1979, pp. 486-493, vol. 27, issue 5.
Schubert, Christine L., et al. "Adjuvants and Volatility of Hormone Herbicides", Pestic. Sci., 1993, pp. 179-183, vol. 38.
International Search Report completed Aug. 1, 2011, in International Application No. PCT/EP2010/064343, filed Sep. 28, 2010.
International Preliminary Report on Patentability dated Jan. 17, 2012, from corresponding International Application No. PCT/EP2010/064343, filed Sep. 28, 2010.
European Search Report from corresponding EP application No. 09173368, completed Apr. 15, 2010.

* cited by examiner

*Primary Examiner* — Clinton Brooks
(74) *Attorney, Agent, or Firm* — Brinks Gilson & Lione

(57) ABSTRACT

The present invention relates to a salt comprising an anionic pesticide and a cationic polyamine of the formula (A) or (B) as described in the description. The invention further relates to an agrochemical composition comprising said salt. It also relates to a method for preparing said salt comprising combining the pesticide in its neutral form or as salt, and the polyamine in its neutral form or as salt. In addition, the invention relates to a method of combating harmful insects and/or phytopathogenic fungi. It also relates to a method of controlling undesired vegetation. Finally, the invention relates to seed comprising said salt.

15 Claims, No Drawings

LOW VOLATILE AMINE SALTS OF ANIONIC PESTICIDES

This application is a National Stage application of International Application No. PCT/EP2010/064343, filed Sept. 28, 2010, which claims the benefit of U.S. Provisional Application No. 61/247,005 filed Sept. 30, 2009, and U.S. Provisional Application No. 61/348,758, filed May 27, 2010, the entire contents of which are hereby incorporated herein by reference. This application also claims priority under 35 U.S.C. §119 to European Patent Application No. 09173368.3, filed Oct. 19, 2009, the entire contents of which is hereby incorporated herein by reference.

The present invention relates to a salt comprising an anionic pesticide and a cationic polyamine of the formula (A) or (B) as described below. The invention further relates to an agrochemical composition comprising said salt. It also relates to a method for preparing said salt comprising combining the pesticide in its neutral form or as salt, and the polyamine in its neutral form or as salt. In addition, the invention relates to a method of combating harmful insects and/or phytopathogenic fungi, which comprises contacting plants seed, soil or habitat of plants in or on which the harmful insects and/or phytopathogenic fungi are growing or may grow, plants, seed or soil to be protected from attack or infestation by said harmful insects and/or phytopathogenic fungi with an effective amount of said agrochemical formulation. It also relates to a method of controlling undesired vegetation, which comprises allowing a herbicidal effective amount of said agrochemical formulation to act on plants, their habitat or on seed of said plants. Finally, the invention relates to seed comprising said salt. The preferred embodiments of the invention mentioned herein below have to be understood as being preferred either independently from each other or in combination with one another.

There are various pesticides which have a rather high volatility, such as free acid forms of carboxylic acid containing pesticides like dicamba or 2,4-D. Such volatile pesticides are subject to a higher degree of drift, which could cause damage to sensitive off-target crops (e.g. soybeans) in nearby fields. They are also less effective on target pests, since a large part of the pesticide evaporates. To avoid these problems, low volatile pesticides are desirable.

Various salts of anionic pesticides are known comprising cationic, amino-functionalized compounds:

U.S. Pat. No. 4,405,531 and WO 97/24931 disclose various organic salts of glyphosate, for examples salts prepared from ethylenediamine, diethylenetriamine, propylenediamine, phenylenediamine or piperidine.

EP 0 183 384 discloses a low volatility salt of dicamba, namely the 2-(2-aminoethoxy)-ethanol salt.

U.S. Pat. No. 5,221,791 discloses aminoalkylpyrrolidone salts of pesticides comprising an acidic hydrogen, such as dicamba.

EP 0 375 624 discloses low volatility amine salts of pesticides, wherein the amine is for example an aminopropylmorpholine, Jeffamine D-230, or 2,4,6-tris(dimethylaminomethyl)phenol.

These amino salts of anionic pesticides are associated with various disadvantages: The starting materials have a rather low boiling point which makes them difficult to handle (such as ethylenediamine Fp 117° C.). Although these pesticide salts have already a lowered volatility compared to the free acid forms of the pesticide, this residual volatility was still too high. Further problems are that some salts have only reduced pesticidal activity, that they are too expensive, and/or that they have a low solubility in water.

Object of the present invention was to find salts of pesticides, which show a low volatility. These salts should be easily preparable starting from cheap, industrially available compounds, which are easy to handle. Another object was that the pesticidal activity remains at a level equivalent to known salts or the free acid of the pesticide. Yet another object was to find salts, which have a high solubility in water.

The object was solved by a salt comprising an anionic pesticide and a cationic polyamine of the formula

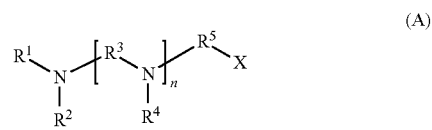

(A)

wherein $R^1$, $R^2$, $R^4$, $R^6$ and $R^7$ are independently H or $C_1$-$C_6$-alkyl, which is optionally substituted with OH, $R^3$ and $R^5$ are independently $C_2$-$C_4$-alkylene, X is OH or $NR^6R^7$, and n is from 1 to 20; or

(B)

wherein $R_{10}$ and $R_{11}$ are independently H or $C_1$-$C_6$-alkyl, $R_{12}$ is $C_1$-$C_{12}$-alkylene, and $R^{13}$ is an aliphatic $C_5$-$C_8$ ring system, which comprises either nitrogen in the ring or which is substituted with at least one unit $NR^{10}R^{11}$. Preferably, the cationic polyamine is of the formula (A).

The term "salt" refers to chemical compounds, which comprise an anion and a cation. The ratio of anions to cations usually depends on the electric charge of the ions. Typically, salts dissociate when dissolved in water in anions and cations.

The term "pesticide" within the meaning of the invention states that one or more compounds can be selected from the group consisting of fungicides, insecticides, nematicides, herbicide and/or safener or growth regulator, preferably from the group consisting of fungicides, insecticides or herbicides, most preferably from the group consisting of herbicides. Also mixtures of pesticides of two or more the aforementioned classes can be used. The skilled artisan is familiar with such pesticides, which can be, for example, found in the Pesticide Manual, 15th Ed. (2009), The British Crop Protection Council, London.

The term "anionic pesticide" refers to a pesticide, which is present as an anion. Preferably, anionic pesticides relate to pesticides comprising a protonizable hydrogen. More preferably, anionic pesticides relate to pesticides comprising a carboxylic, thiocarbonic, sulfonic, sulfinic, thiosulfonic or phosphorous acid group, especially a carboxylic acid group. The aforementioned groups may be partly present in neutral form including the protonizable hydrogen.

Usually, anions such as anionic pesticides comprise at least one anionic group. Preferably, the anionic pesticide comprises one or two anionic groups. In particular the anionic pesticide comprises exactly one anionic group. An example of an anionic group is a carboxylate group (—C(O)O⁻). The aforementioned anionic groups may be partly present in neutral form including the protonizable hydrogen. For example, the carboxylate group may be present partly in neutral form of carboxylic acid (—C(O)OH). This is preferably the case in aqueous compositions, in which an equilibrium of carboxylate and carboxylic acid may be present.

Suitable anionic pesticides are given in the following. In case the names refer to a neutral form or a salt of the anionic pesticide, the anionic form of the anionic pesticides are meant. For example, the anionic form of dicamba may be represented by the following formula:

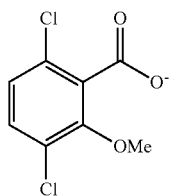 [SMILES: COc1c(Cl)ccc(Cl)c1C(=O)[O-]]

As another example, the anionic form of glyphosate may be represented by the following formula:

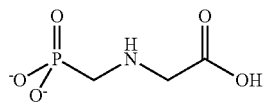

Suitable anionic pesticides are herbicides, which comprise a carboxylic, thiocarbonic, sulfonic, sulfinic, thiosulfonic or phosphorous acid group, especially a carboxylic acid group. Examples are aromatic acid herbicides, phenoxycarboxylic acid herbicides or organophosphorus herbicides comprising a carboxylic acid group.

Suitable aromatic acid herbicides are benzoic acid herbicides, such as diflufenzopyr, naptalam, chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, ciopyralid, picloram; quinolinecarboxylic acid herbicides, such as quinclorac, quinmerac; or other aromatic acid herbicides, such as aminocyclopyrachlor. Preferred are benzoic acid herbicides, especially dicamba.

Suitable phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxyphenoxypropionic herbicides, such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop. Preferred are phenoxyacetic herbicides, especially MCPA.

Suitable organophosphorus herbicides comprising a carboxylic acid group are bialafos, glufosinate, glufosinate-P, glyphosate. Preferred is glyphosate.

Suitable other herbicides comprising a carboxylic acid are pyridine herbicides comprising a carboxylic acid, such as fluoroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron; imidazolinone herbicides, such as imazamethabenz, imazamethabenz, imazamox, imazapic, imazapyr, imazaquin and imazethapyr; triazolinone herbicides such as flucarbazone, propoxycarbazone and thien carbazone; aromatic herbicides such as acifluorfen, bifenox, carfentrazone, flufenpyr, flumiclorac, fluoroglycofen, fluthiacet, lactofen, pyraflufen. Further on, chlorflurenol, dalapon, endothal, flamprop, flamprop-M, flupropanate, flurenol, oleic acid, pelargonic acid, TCA may be mentioned as other herbicides comprising a carboxylic acid.

Suitable anionic pesticides are fungicides, which comprise a carboxylic, thiocarbonic, sulfonic, sulfinic, thiosulfonic or phosphorous acid group, especially a carboxylic acid group. Examples are polyoxin fungicides, such as polyoxorim.

Suitable anionic pesticides are insecticides, which comprise a carboxylic, thiocarbonic, sulfonic, sulfinic, thiosulfonic or phosphorous acid group, especially a carboxylic acid group. Examples are thuringiensin.

Suitable anionic pesticides are plant growth regulator, which comprise a carboxylic, thiocarbonic, sulfonic, sulfinic, thiosulfonic or phosphorous acid group, especially a carboxylic acid group. Examples are 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, preferably prohexadione and trinexapac.

Preferred anionic pesticides are anionic herbicides, more preferably dicamba, glyphosate, 2,4-D, aminopyralid, aminocyclopyrachlor and MCPA. Especially preferred are dicamba and glyphosate. In another preferred embodiment, dicamba is preferred. In another preferred embodiment, 2,4-D is preferred. In another preferred embodiment, glyphosate is preferred. In another preferred embodiment, MCPA is preferred.

In a preferred embodiment the salt comprises an anionic pesticide, wherein all anionic groups of said anionic pesticide are selected from one or more carboxylate groups (pesticide A1). More preferably, the anionic pesticide comprises one anionic group, which is a carboxylate group, or it comprises two anionic groups, which are both carboxylate groups. In particular, the anionic pesticide comprises exactly one anionic group, which is a carboxylate group.

When all anionic groups of the anionic pesticide are selected from one or more carboxylate groups, the anionic pesticide is free of anionic groups beside carboxylate groups. For example, it is free of thiocarboxylic, sulfonate, sulfininate, thiosulfonate or phosphonate groups.

Suitable pesticides A1 are given in the following. In case the names refer to a neutral form or a salt of the pesticide, the anionic form of the pesticides is meant.

Preferred pesticides A1 are herbicides, such as aromatic acid herbicides, or phenoxycarboxylic acid herbicides.

Preferred herbicides are clopyralid, picloram, quinclorac, quinmerac, dicamba, 2,4-dichlorophenoxy)acetic acid (2,4-D), 4-(4-chloro-o-tolyloxy)butyric acid (MCPA), 4-(4-chloro-o-tolyloxy)butyric acid (MCPB), dichlorprop, dichlorprop-P, mecoprop, mecoprop-P, fluoroxypyr, triclopyr.

Suitable aromatic acid herbicides are benzoic acid herbicides, such as chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, clopyralid, picloram; quinolinecarboxylic acid herbicides, such as quinclorac, quinmerac; or other aromatic acid herbicides, such as aminocyclopyrachlor. Preferred are benzoic acid herbicides, especially dicamba.

Suitable phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxyphenoxypropionic herbicides, such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop. Preferred are phenoxyacetic herbicides, especially MCPA.

Suitable other herbicides comprising a carboxylic acid are pyridine herbicides comprising a carboxylic acid, such as fluoroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron.

Further suitable pesticides A1 are fungicides, such as polyoxin fungicides (e.g. polyoxorim).

Further suitable pesticides A1 are insecticides, such as thuringiensin.

Suitable anionic pesticides are plant growth regulator, such as 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, wherein prohexadione and trinexapac are more preferred.

Most preferred pesticides A1 are dicamba, 2,4-D, aminopyralid, aminocyclopyrachlor and MCPA. Especially preferred is dicamba. In another preferred embodiment, 2,4-D is preferred. In another preferred embodiment, MCPA is preferred.

In another preferred embodiment, the salt comprises an anionic pesticide, wherein at least one anionic group of said anionic pesticide is selected from one or more phosphonate groups (pesticide A2). Preferred pesticides A2 are herbicides, wherein at least one anionic group of said herbicide is selected from one or more phosphonate groups. Examples are organophosphorus herbicides comprising a carboxylic acid group. Suitable organophosphorus herbicides comprising a carboxylic acid, group are bilanafos, glufosinate, glufosinate-P, glyphosate. Preferred is pesticide A2 is glyphosate.

In a preferred embodiment, the present invention relates to a salt comprising an anionic pesticide, wherein all anionic groups of said anionic pesticide are selected from one or more carboxylate groups (pesticide A1), and a cationic polyamine (B) of the formula (B1)

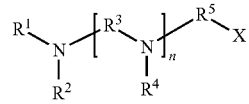

(B1)

wherein $R^1$, $R^2$, $R^4$, $R^6$ and $R^7$ are independently H or $C_1$-$C_6$-alkyl, which is optionally substituted with OH, $R^3$ and $R^5$ are independently $C_2$-$C_4$-alkylene, X is OH or $NR^6R^7$, and n is from 1 to 20;

or of the formula (B2)

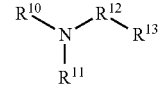

(B2)

wherein $R^{10}$ and $R^{11}$ are independently H or $C_1$-$C_6$-alkyl, $R^{12}$ is $C_1$-$C_{12}$-alkylene, and $R^{13}$ is an aliphatic $C_5$-$C_8$ ring system, which comprises either nitrogen in the ring or which is substituted with at least one unit $NR^{10}R^{11}$.

The term "polyamine" within the meaning of the invention relates to an organic compound comprising at least two amino groups, such as an primary, secondary or tertiary amino group.

The term "cationic polyamine" refers to a polyamine, which is present as cation. Preferably, in a cationic polyamine at least one amino group is present in the cationic form of an ammonium, such as R—$N^+H_3$, $R_2$—$N^+H_2$, or $R_3$—$N^+H$. When formulae, such as (B1), (B2), (B3) or (B4), show neutral molecules, they usually refer to their cationic form (i.e. at least one amino group is present in the cationic form of an ammonium, such as R—$N^+H_3$, $R_2$—$N^+H_2$, or $R_3$—$N^+H$). For example, the cationic form of B1.1 may be represented by at least one of the following formulae:

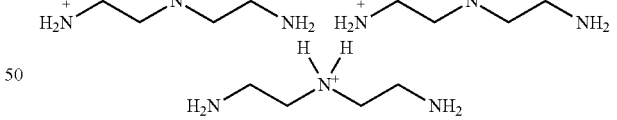

For example, the cationic form of B1.2 may be represented by at least one of the following formulae:

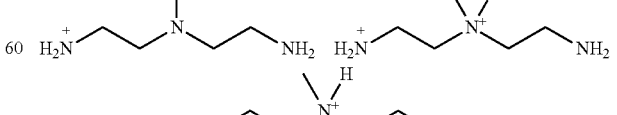

For example, the cationic form of B1.6 may be represented by at least one of the following formulae:

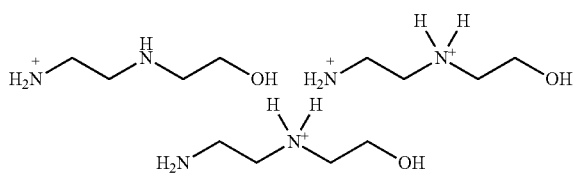

An expert is aware which of the amine groups in the cationic polyamine is preferably protonated, because this depends for example on the pH or the physical form. In aqueous solutions the alkalinity of the amino groups of the cationic polyamine increases usually from tertiary amine to primary amine to secondary amine.

In an embodiment the cationic polyamine has the formula

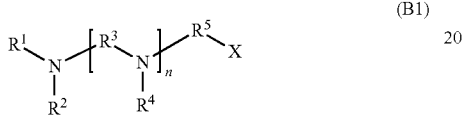
(B1)

wherein $R^1$, $R^2$, $R^4$, $R^6$, $R^7$ are independently H or $C_1$-$C_6$-alkyl, which is optionally substituted with OH, $R^3$ and $R^5$ are independently $C_2$-$C_{10}$-alkylene, X is OH or $NR^6R^7$, and n is from 1 to 20. $R^1$, $R^2$, $R^4$, $R^6$ and $R^7$ are preferably independently H or methyl. Preferably, $R^1$, $R^2$, $R^6$ and $R^7$ are H. $R^6$ and $R^7$ are preferably identical to $R^1$ and $R^2$, respectively. $R^3$ and $R^5$ are preferably independently $C_2$-$C_3$-alkylene, such as ethylene (—$CH_2CH_2$—), or n-propylene (—$CH_2CH_2CH_2$—). Typically, $R^3$ and $R^5$ are identical. $R^3$ and $R^5$ may be linear or branched, unsubstituted or substituted with halogen. Preferably, $R^3$ and $R^5$ are linear. Preferably, $R^3$ and $R^5$ are unsubstituted. X is preferably $NR^6R^7$. Preferably, n is from 1 to 10, more preferably from 1 to 6, especially from 1 to 4. In another preferred embodiment, n is from 2 to 10. Preferably, $R^1$, $R^2$, and $R^4$ are independently H or methyl, $R^3$ and $R^5$ are independently $C_2$-$C_3$-alkylene, X is OH or $NR^6R^7$, and n is from 1 to 10.

The group X is bound to $R^5$, which is a $C_2$-$C_{10}$-alkylene group. This means that X may be bound to any carbon atom of the $C_2$-$C_{10}$-alkylene group. Examples of a unit —$R^5$—X are —$CH_2$—$CH_2$—$CH_2$—OH or —$CH_2$—CH(OH)—$CH_3$.

$R^1$, $R^2$, $R^4$, $R^6$, $R^7$ are independently H or $C_1$-$C_6$-alkyl, which is optionally substituted with OH. An example such a substitution is formula (B1.9), in which $R^4$ is H or $C_1$-$C_6$-alkyl substituted with OH (more specifically, $R^4$ is $C_3$-alkyl substituted with OH. Preferably, $R^1$, $R^2$, $R^4$, $R^6$, $R^7$ are independently H or $C_1$-$C_6$-alkyl.

In another preferred embodiment the cationic polymer of the formula (B1) is free of ether groups (—O—). Ether groups are known to enhance photochemical degradation resulting in explosive radicals or peroxy groups.

Examples for cationic polyamines of the formula (B1) wherein X is $NR^6R^7$ are diethylenetriamine (DETA, (B4) with k=1, corresponding to (B1.1)), triethylenetetraamine (TETA, (B4) with k=2), tetraethylenepentaamine (TEPA, (B4) with k=3). Technical qualities of TETA are often mixtures comprising in addition to linear TETA as main component also tris-aminoethylamine TAEA, piperazinoethylethylenediamine PEEDA and Diaminoethylpiperazine DAEP. Technical qualities of TEPA a are often mixtures comprising in addition to linear TEPA as main component also aminoethyltris-aminoethylamine AE-TAEA, aminoethyldiaminoethylpiperazine AE-DAEP and aminoethylpiperazinoethylethylenediamine AE-PEEDA. Such ethyleneamines are commercially available from Dow Chemical Company. Further examples are Pentamethyldiethylenetriamine PMDETA (B1.3), N,N,N',N'',N''-pentamethyl-dipropylenetriamine (B1.4) (commercially available as Jeffcat® ZR-40), N,N-bis(3-dimethylaminopropyl)-N-isopropanolamine (commercially available as Jeffcat® ZR-50), N'-(3-(dimethylamino)-propyl)-N,N-dimethyl-1,3-propanediamine (B1.5) (commercially available as Jeffcat® Z-130), and N,N-Bis(3-aminopropyl)methylamine BAPMA (B1.2). Especially preferred are (B4), wherein k is from 1 to 10, (B1.2), (B1.4) and (B1.5). Most preferred are (B4), wherein k is 1, 2, 3, or 4 and (B1.2). In particular preferred are (B1.1) and (B1.2).

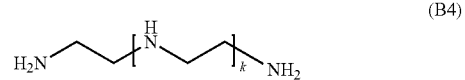
(B4)

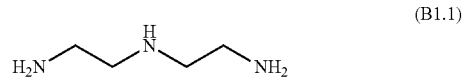
(B1.1)

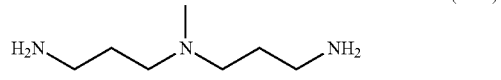
(B1.2)

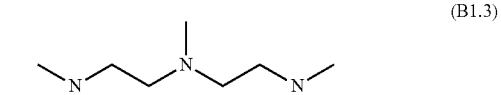
(B1.3)

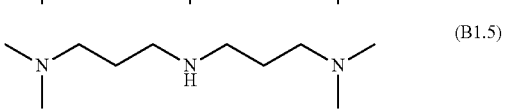
(B1.4)

(B1.5)

Examples for polyamines of the formula (B1) wherein X is OH are N-(3-dimethylaminopropyl)-N,N-diisopropanolamine DPA (B1.9), N,N,N'-trimethylaminoethyl-ethanolamine (B1.7) (commercially available as Jeffcat® Z-110), aminopropylmonomethylethanolamine APMMEA (B1.8), and aminoethylethanolamine AEEA (B1.6). Especially preferred is (B1.6).

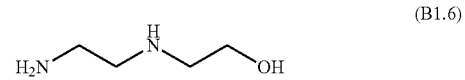
(B1.6)

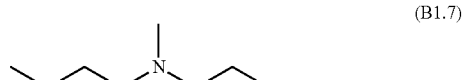
(B1.7)

(B1.8)

-continued (B1.9)
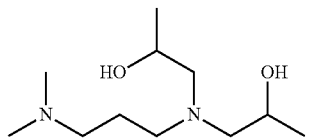

In another embodiment the cationic polyamine has the formula (B2)
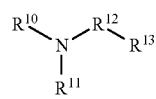

wherein $R^{10}$ and $R^{11}$ are independently H or $C_1$-$C_6$-alkyl, $R^{12}$ is $C_2$-$C_{12}$-alkylene, and $R^{13}$ is an aliphatic $C_5$-$C_8$ ring system, which comprises either nitrogen in the ring or which is substituted with at least one unit $NR^{10}R^{11}$.

$R^{10}$ and $R^{11}$ are preferably independently H or methyl, more preferably H. Typically $R^{10}$ and $R^{11}$ are linear or branched, unsubstituted or substituted with halogen. Preferably, $R^{10}$ and $R^{11}$ are unsubstituted and linear. More preferably, $R^{10}$ and $R^{11}$ are identical.

$R^{12}$ is preferably $C_2$-$C_4$-alkylene, such as ethylene (—$CH_2CH_2$—), or n-propylene (—$CH_2CH_2CH_2$—). $R^{12}$ may be linear or branched, preferably it is linear. $R^{12}$ may be unsubstituted or substituted with halogen, preferably it is unsubstituted.

$R^{13}$ is an aliphatic $C_5$-$C_8$ ring system, which comprises either nitrogen in the ring or which is substituted with at least one unit $NR^{10}R^{11}$. Preferably, $R^{13}$ is an aliphatic $C_5$-$C_8$ ring system, which comprises nitrogen in the ring. The $C_5$-$C_8$ ring system may be unsubstituted or substituted with at least one $C_1$-$C_6$ alkyl group or at least one halogen. Preferably, the $C_5$-$C_8$ ring system is unsubstituted or substituted with at least one $C_1$-$C_4$ alkyl group. Examples for an aliphatic $C_5$-$C_8$ ring system, which comprises nitrogen in the ring, are piperazyl groups. Examples for $R^{13}$ being an aliphatic $C_5$-$C_8$ ring system, which comprises nitrogen in the ring, are the compounds of the formula (B2.11) and (B2.12) below. Examples for $R^{13}$ being an aliphatic $C_5$-$C_8$ ring system, which is substituted with at least one unit $NR^{10}R^{11}$ is the compound of the formula (B2.10) below.

More preferably, $R^{10}$ and $R^{11}$ are independently H or methyl, $R^{12}$ is $C_2$-$C_3$-alkylene, and $R^{13}$ is an aliphatic $C_5$-$C_8$ ring system, which comprises oxygen or nitrogen in the ring. In another preferred embodiment the cationic polymer of the formula (B2) is free of ether groups (—O—).

Especially preferred cationic polyamines of formula (B2) are isophorone diamine ISPA (B2.10), aminoethylpiperazine AEP (B2.11), and 1-methyl-4-(2-dimethylaminoethyl)-piperazine TAP (B2.12). These compounds are commercially available from Huntsman or Dow, USA. Preferred are (B2.10) and (B2.11), more preferably (B2.11). In another embodiment (B2.11) and (B2.12) are preferred.

(B2.10)
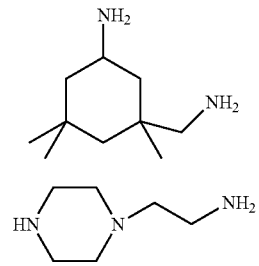

(B2.11)
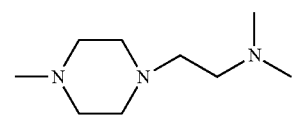

(B2.12)
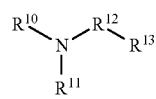

The salt according to the invention, which comprises pesticide A1, is more preferably selected from a salt comprising dicamba and (B1), dicamba and (B2), dicamba and (B3), or dicamba and (B4). The salt is most preferably selected from a salt comprising dicamba and (B1.1), dicamba and (B1.2), dicamba and (B1.3), dicamba and (B1.4), dicamba and (B1.5), dicamba and (B1.6), dicamba and (B1.7), dicamba and (B1.8), dicamba and (B1.9), dicamba and (B1.10), dicamba and (B1.11), or dicamba and (B1.12). The salt according to the invention is particularly preferred selected from a salt comprising dicamba and polyamine (B1.1), dicamba and polyamine (B1.2), 2,4-D and polyamine (B1.1), or 2,4-D and polyamine (B1.2). Particularly, the salt comprises dicamba and polyamine (B1.1). In a further particular embodiment, the salt comprises dicamba and polyamine (B1.2).

In a further preferred embodiment, the present invention relates to a salt comprising an anionic pesticide, wherein at least one anionic group of said anionic pesticide is selected from one or more phosphonate groups (pesticide A2), and a cationic polyamine of the formula (B1.2), or (B1.5)

(B1.2)
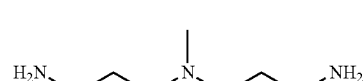

(B1.5)
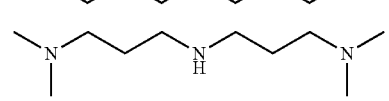

or of the formula (B3)

(B3)
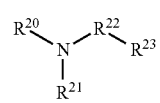

wherein $R^{20}$ and $R^{21}$ are independently H or $C_1$-$C_6$-alkyl,
$R^{22}$ is $C_1$-$C_{12}$-alkylene, and
$R^{23}$ is an aliphatic $C_5$-$C_8$ ring system, which comprises either nitrogen in the ring or which is substituted with at least one unit $NR^{20}R^{21}$.

$R^{20}$ and $R^{21}$ are preferably independently H or methyl, more preferably H. Typically $R^{20}$ and $R^{21}$ are linear or branched, unsubstituted or substituted with halogen. Preferably, $R^{20}$ and $R^{21}$ are unsubstituted and linear. More preferably, $R^{20}$ and $R^{21}$ are identical.

$R^{22}$ is preferably $C_2$-$C_4$-alkylene, such as ethylene (—$CH_2CH_2$—), or n-propylene (—$CH_2CH_2CH_2$—). $R^{22}$ may be linear or branched, preferably it is linear. $R^{22}$ may be unsubstituted or substituted with halogen, preferably it is unsubstituted.

$R^{23}$ is an aliphatic $C_5$-$C_8$ ring system, which comprises either nitrogen in the ring or which is substituted with at least one unit $NR^{20}R^{21}$. Preferably, $R^{23}$ is an aliphatic $C_5$-$C_8$ ring system, which comprises nitrogen in the ring. The $C_5$-$C_8$ ring system may be unsubstituted or substituted with at least one $C_1$-$C_6$ alkyl group or at least one halogen. Preferably, the $C_5$-$C_8$ ring system is unsubstituted or substituted with at least one $C_1$-$C_4$ alkyl group. Examples for an aliphatic $C_5$-$C_8$ ring system, which comprises nitrogen in the ring, are piperazyl groups. Examples for $R^{23}$ being an aliphatic $C_5$-$C_8$ ring system, which comprises nitrogen in the ring, are the compounds of the formula (82.11) and (B2.12) below. Examples for $R^{23}$ being an aliphatic $C_5$-$C_8$ ring system, which is substituted with at least one unit $NR^{20}R^{21}$ is the compound of the formula (B2.10) below.

More preferably, $R^{20}$ and $R^{21}$ are independently H or methyl, $R^{22}$ is $C_2$-$C_3$-alkylene, and $R^{23}$ is an aliphatic $C_5$-$C_8$ ring system, which comprises oxygen or nitrogen in the ring. In another preferred embodiment the cationic polymer of the formula (B) is free of ether groups (—O—).

Especially preferred cationic polyamines of formula (B3) are isophorone diamine ISPA (B2.10), aminoethylpiperazine AEP (B2.11), and 1-methyl-4-(2-dimethylaminoethyl)-piperazine TAP (B2.12). These compounds are commercially available from Huntsman or Dow, USA. Preferred are (B2.10) and (B2.11), more preferably (B2.11). In another embodiment (B2.11) and (B2.12) are preferred.

Cationic Polyamines of the formula (B1), (B2) and (B3) are obtainable by known methods or even commercially available.

The salt according to the invention, which comprises pesticide A2, is more preferably selected from a salt comprising glyphosate and (B1.2), glyphosate and (B1.5), or glyphosate and (B3). The salt is most preferably selected from a salt comprising glyphosate and (B1.1), glyphosate and (B1.5), glyphosate and (B1.10), glyphosate and (B1.11), or glyphosate and (B1.12).

The present invention also relates to a method for preparing the salt according to the invention comprising combining the pesticide in its neutral form or as salt, and the polyamine in its neutral form or as salt. The pesticide and the polyamine may be combined either neatly or with the compound in its available formulation, for example, dry or solid formulations as well as liquid formulations such as aqueous formulations. Preferably, the pesticide and the polyamine are contacted in water. More preferably, the pesticide or the polyamine, respectively, is neutralized in aqueous solution by addition of the polyamine or the pesticide, respectively. The water may be removed after the combining for isolation of the salt. The combination may be done at usual temperature for preparing salts, such as from −20° C. to 100° C.

The pesticide and the polyamine may be combined in a variety of molar ratios, which depend on the number of electric charges of the ions. For example, one mol of an anionic pesticides comprising one negative charge per mol is usually combined with one mol of cationic polyamine comprising one positive charge per mol. Preferably, the pesticide and the polyamine are combined in such a molar ratio which results to a pH of 6.5 to 9.0, preferably 7.0 to 8.0, when the salt is present in water at 20° C. at a concentration of 480 g/l. In a further embodiment, the pesticide and the polyamine may be combined in a molar ratio in the range from 1/10 to 10/1, preferably from 1/4 to 4/1, more preferably from 1/2 to 2/1.

The present invention further relates to an agrochemical composition comprising the salt according to the invention. In another embodiment, the present invention further relates to an agrochemical composition comprising at least one salt according to the invention. For example, the agrochemical composition may comprise one, two or three salts according to the invention, wherein it comprises preferably one salt according to the invention.

In the agrochemical composition according to the invention several anionic pesticides, such as two or three, may be present. For example, the composition may comprise at least two anionic pesticides selected from dicamba, quinclorac, glyphosate, 2,4-D, aminopyralid and MCPP. More preferably, it may comprise at least dicamba and glyphosate, 2,4-D and dicamba, dicamba and 2,4-D and MCPP, or aminopyralid and 2,4-D and glyphosate.

The agrochemical composition may comprise at least one further pesticide. The further pesticide can be selected from the group consisting of fungicides, insecticides, nematicides, herbicide and/or safener or growth regulator, preferably from the group consisting of fungicides, insecticides or herbicides, more preferably herbicides. Preferred further pesticides are imidazolinone herbicides and triazine herbicides.

The following list give examples of pesticides which may be used as further pesticide. Preferred further pesticides from this list are those which are not anionic pesticides.

Examples for fungicides are:

A) Strobilurins
   azoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

B) Carboxamides
   carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methylthiazole-5-carboxanilide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide;
   carboxylic morpholides: dimethomorph, flumorph, pyrimorph;
   benzoic acid amides: flumetover, fluopicolide, fluopyram, zoxamide;
   other carboxamides: carpropamid, dicyclomet, mandiproamid, oxytetracyclin, silthiofarm and N-(6-methoxy-pyridin-3-yl)cyclopropanecarboxylic acid amide;

C) Azoles
   triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;

imidazoles: cyazofamid, imazalil, pefurazoate, prochloraz, triflumizol;

benzimidazoles: benomyl, carbendazim, fuberidazole, thiabendazole;

others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D) Heterocyclic Compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydropyrazole-1-carbothioic acid S-allyl ester;

others: acibenzolar-5-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propyl-chromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine;

E) Carbamates thio- and dithiocarbamates: ferbam, mancozeb, maneb, metam, methasulphocarb, metiram, propineb, thiram, zineb, ziram;

carbamates: benthiavalicarb, diethofencarb, iprovalicarb, propamocarb, propamo-1-carb hydrochlorid, valifenalate and N-(1-(1-(4-cyano-phenyl)ethanesulfonyl)-but-2-yl)carbamic acid-(4-fluorophenyl)ester;

F) Other Active Substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methylbenzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tebufloquin, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethylphenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxyacetic acid 6-tertbutyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Examples for Growth Regulators are:

Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole.

Examples for Herbicides are:

acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate (e.g. glyphosate free acid, glyphosate ammonium salt, glyphosate isopropylammonium salt, glyphosate trimethylsulfonium salt, glyphosate potassium salt, glyphosate dimethylamine salt), glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, Drechslera monoceras, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chlorophenyl)-5-fluoropyridine-2-carboxylic acid, 4-amino-3-chloro-6-(4-chloro-2-fluoro-3-methoxyphenyl)-pyridine-2-carboxylic acid methyl ester, and 4-amino-3-chloro-6-(4-chloro-3-dimethylamino-2-fluorophenyl)-pyridine-2-carboxylic acid methyl ester.

Examples for Insecticides are:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

In an further embodiment, the present invention relates to a herbicidally active composition comprising A) at least one anionic pesticide (preferably pesticide A1 (such as dicamba); or in another embodiment pesticide A2 (such as glyphosate))

and at least one further active compound selected from

C) herbicides of class c1) to c15):

c1) lipid biosynthesis inhibitors;
c2) acetolactate synthase inhibitors (ALS inhibitors)
c3) photosynthesis inhibitors;
c4) protoporphyrinogen-IX oxidase inhibitors,
c5) bleacher herbicides;
c6) enolpyruvyl shikimate 3-phosphate synthase inhibitors (EPSP inhibitors);
c7) glutamine synthetase inhibitors;

c8) 7,8-dihydropteroate synthase inhibitors (DHP inhibitors);
c9) mitose inhibitors;
c10) inhibitors of the synthesis of very long chain fatty acids (VLCFA inhibitors);
c11) cellulose biosynthesis inhibitors;
c12) decoupler herbicides;
c13) auxin herbicides;
c14) auxin transport inhibitors; and
c15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenolbutyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives; and
D) safeners.

The invention relates in particular to compositions in the form of herbicidally active crop protection compositions comprising a herbicidally effective amount of an active compound combination comprising at least one anionic pesticide and at least one further compound selected from the herbicides C and the safeners D, as defined above, and also at least one liquid and/or solid carrier and/or one or more surfactants and, if desired, one or more further auxiliaries customary for crop protection compositions.

The invention also relates to compositions in the form of a crop protection composition formulated as a 1-component composition comprising an active compound combination comprising at least one anionic pesticide and at least one further active compound selected from the herbicides C and the safeners D, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one anionic pesticide, a solid or liquid carrier and/or one or more surfactants, and a second component comprising at least one further active compound selected from the herbicides C and safeners D, a solid or liquid carrier and/or one or more surfactants, where additionally both components may also comprise further auxiliaries customary for crop protection compositions.

Surprisingly, the compositions according to the invention comprising at least one anionic pesticide and at least one herbicide C have better herbicidal activity, i.e. better activity against harmful plants, than would have been expected based on the herbicidal activity observed for the individual compounds, or a broader activity spectrum. The herbicidal activity to be expected for mixtures based on the individual compound can be calculated using Colby's formula (see below). If the activity observed exceeds the expected additive activity of the individual compounds, synergism is said to be present.

Moreover, the time frame, within which the desired herbicidal action can be achieved, may be expanded by the compositions according to the invention comprising at least one anionic pesticide and at least one herbicide C and optionally a safener D. This allows a more flexibly timed application of the compositions according to the present invention in comparison with the single compounds.

The compositions according to the invention comprising both at least anionic pesticide and at least one of the compounds mentioned under D also have good herbicidal activity against harmful plants and better compatibility with useful plants.

Surprisingly, the compositions according to the invention comprising at least one anionic pesticide, at least one herbicide C and at least one of the compounds mentioned under D have better herbicidal activity, i.e. better activity against harmful plants, than would have been expected based on the herbicidal activity observed for the individual compounds, or a broader activity spectrum, and show better compatibility with useful plants than compositions comprising only one compound I and one herbicide C.

In one embodiment of the present invention the compositions according to the present invention comprise at least one anionic pesticide and at least one further active compound C (herbicide C).

According to a first embodiment of the invention the compositions contain at least one inhibitor of the lipid biosynthesis (herbicide c1). These are compounds which inhibit lipid biosynthesis. Inhibition of the lipid biosynthesis can be affected either through inhibition of acetyl CoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a second embodiment of the invention the compositions contain at least one ALS inhibitor (herbicide c2). The herbicidal activity of these compounds is based on the inhibition of acetolactate synthase and thus on the inhibition of the branched chain aminoacid biosynthesis. These inhibitors belong to the group C of the HRAC classification system.

According to a third embodiment of the invention the compositions contain at least one inhibitor of photosynthesis (herbicide c3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to a fourth embodiment of the invention the compositions contain at least one inhibitor of protoporphyrinogen-IX-oxidase (herbicide c4). The herbicidal activity of these compounds is based on the inhibition of the protoporphyrinogen-IX-oxidase. These inhibitors belong to the group E of the HRAC classification system.

According to a fifth embodiment of the invention the compositions contain at least one bleacher-herbicide (herbicide c5). The herbicidal activity of these compounds is based on the inhibition of the carotinoid biosynthesis. These include compounds which inhibit carotinoid biosynthesis by inhibition of phytoene desaturase (so-called PDS inhibitors, group F1 of HRAC classification), compounds which inhibit the 4-hydroxyphenylpyruvat-dioxygenase (HPPD inhibitors, group F2 of HRAC classification) and compounds which inhibit carotinoid biosynthesis by an unknown mode of action (bleacher—unknown target, group F3 of HRAC classification).

According to a sixth embodiment of the invention the compositions contain at least one EPSP synthase inhibitor (herbicide c6). The herbicidal activity of these compounds is based on the inhibition of enolpyruvyl shikimate 3-phosphate synthase und thus on the inhibition of the aminoacid biosynthesis in plants. These inhibitors belong to the group G of the HRAC classification system.

According to a seventh embodiment of the invention the compositions contain at least one glutamin synthetase inhibitor (herbicide c7). The herbicidal activity of these compounds is based on the inhibition of glutamin synthetase und thus on the inhibition of the aminoacid biosynthesis in plants. These inhibitors belong to the group H of the HRAC classification system.

According to an eighth embodiment of the invention the compositions contain at least one DHP synthase inhibitor (herbicide c8). The herbicidal activity of these compounds is based on the inhibition of 7,8-dihydropteroate synthetase. These inhibitors belong to the group I of the HRAC classification system.

According to a ninth embodiment of the invention the compositions contain at least one mitose inhibitor (herbicide c9). The herbicidal activity of these compounds is based on the disturbance or inhibition of microtubule formation or organization and thus on the mitosis inhibition. These inhibitors belong to the groups K1 and K2 of the HRAC classification system. Among these, compounds of the group K1, in particular dinitroanilines, are preferred.

According to a tenth embodiment of the invention the compositions contain at least one VLCFA inhibitor (herbicide c10). The herbicidal activity of these compounds is based on the inhibition of the synthesis of very long chain fatty acids and thus on the disturbance or inhibition of cell division in plants. These inhibitors belong to the group K3 of the HRAC classification system.

According to an eleventh embodiment of the invention the compositions contain at least one cellulose biosynthesis inhibitor (herbicide c11). The herbicidal activity of these compounds is based on the inhibition of the biosynthesis of cellulose and thus on the inhibition of the synthesis of cell walls in plants. These inhibitors belong to the group L of the HRAC classification system.

According to a twelfth embodiment of the invention the compositions contain at least one decoupler herbicide (herbicide c12). The herbicidal activity of these compounds is based on the disruption of the cell membrane. These inhibitors belong to the group M of the HRAC classification system.

According to a thirteenth embodiment of the invention the compositions contain at least one auxin herbicide (herbicide c13). These include compounds which act like auxins, i.e. plant hormones, and inhibit the growth of the plants. These compounds belong to the group O of the HRAC classification system.

According to a fourteenth embodiment of the invention the compositions contain at least one auxin transport inhibitor (herbicide c14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www.plantprotection.org/hrac/MOA.html).

Preference is given to those compositions according to the present invention comprising at least one herbicide C selected from herbicides of class c2, c3, c4, c5, c6, c9 and c10.

Particular preference is given to those compositions according to the present invention which comprise at least one herbicide C selected from the herbicides of class c4, c6 and c10.

Examples of herbicides C which can be used in combination with the anionic pesticide according to the present invention (preferably pesticide A1 (such as dicamba); or in another embodiment pesticide A2 (such as glyphosate)) are:

c1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPIC, esprocarb, ethofumesate, flupropanate, molinate, orbencarb, pebulate, prosulfocarb, TCA, thiobencarb, tiocarbazil, triallate and vernolate;

c2) from the group of the ALS inhibitors:
Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuronmethyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8) and sulfonylaminocarbonyltriazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those compositions comprising at least one imidazolinone herbicide;

c3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridatre, pyridafol, pentanochlor and propanil and inhibitors of the photosystem I such as diquat, diquatdibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

c4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

c5) from the group of the bleacher herbicides:

PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole, clomazone and flumeturon;

c6) from the group of the EPSP synthase inhibitors:

glyphosate, glyphosate-isopropylammonium and glyphosate-trimesium (sulfosate);

c7) from the group of the glutamine synthase inhibitors:

bilanaphos (bialaphos), bilanaphos-sodium, glufosinate, glufosinate-P and glufosinate-ammonium;

c8) from the group of the DHP synthase inhibitors:

asulam;

c9) from the group of the mitose inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

c10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napropamide, tetrazolinones such fentrazamide, and other herbicides such as anilofos, cafenstrole, fenoxasulfone, ipfencarbazone, piperophos, pyroxasulfone and isoxazoline compounds of the formula II,

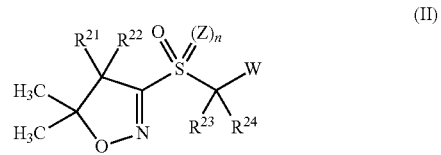

(II)

wherein $R^{21}$, $R^{22}$, $R^{23}$, $R^{24}$, W, Z and n have the following meanings:

$R^{21}$, $R^{22}$, $R^{23}$, $R^{24}$ independently of one another hydrogen, halogen or $C_1$-$C_4$-alkyl;

W phenyl or monocyclic 5-, 6-, 7-, 8-, 9- or 10-membered heterocyclyl containing, in addition to carbon ring members one two or three same or different heteroatoms selected from oxygen, nitrogen and sulfur as ring members, wherein phenyl and heterocyclyl are unsubstituted or carry 1, 2 or 3 substituents $R^{yy}$ selected from halogen $C_1$-$C_4$-alkyl, $C_1$-$C_4$-alkoxy, $C_1$-$C_4$-haloalkyl and $C_1$-$C_4$-haloalkoxy;

preferably phenyl or 5- or 6-membered aromatic heterocyclyl(hetaryl) which contains, in addition to carbon ring members, one, two or three nitrogen atoms as ring members, wherein phenyl and hetaryl are unsubstituted or carry 1, 2 or 3 substituents $R^{yy}$;

Z oxygen or NH; and n zero or one;

among the isoxazoline compounds of the formula II, preference is given to isoxazoline compounds of the formula II, wherein $R^{21}$, $R^{22}$, $R^{23}$, $R^{24}$ independently of one another are H, F, Cl or methyl;

Z is oxygen;

n is 0 or 1; and

W is phenyl, pyrazolyl or 1,2,3-triazolyl, wherein the three last-mentioned radicals are unsubstituted or carry one two or three substituents $R^{yy}$, especially one of the following radicals

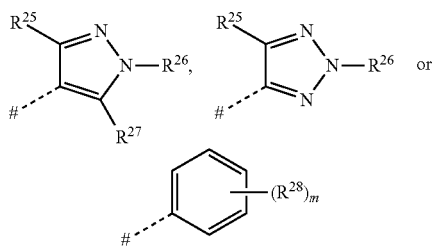

wherein
$R^{22}$ is halogen, $C_1$-$C_4$-alkyl or $C_1$-$C_4$-haloalkyl;
$R^{26}$ is $C_1$-$C_4$-alkyl;
$R^{27}$ is halogen, $C_1$-$C_4$-alkoxy or $C_1$-$C_4$-haloalkoxy;
$R^{28}$ is halogen, $C_1$-$C_4$-alkyl, $C_1$-$C_4$-haloalkyl or $C_1$-$C_4$-haloalkoxy;
m is 0, 1, 2 or 3; and
# denotes the point of attachment to the group $CR^{23}R^{24}$;
among the isoxazoline compounds of the formula II, particular preference is given to those isoxazoline compounds of the formula II, wherein
$R^{21}$ is hydrogen;
$R^{22}$ is fluorine;
$R^{23}$ is hydrogen or fluorine;
$R^{24}$ is hydrogen or fluorine;
W is one of the radicals of the formulae $W^1$, $W^2$, $W^3$ or $W^4$

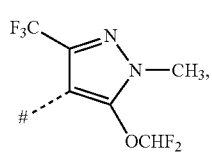 W¹

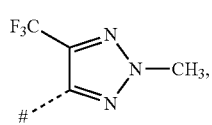 W²

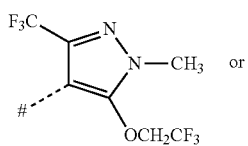 W³

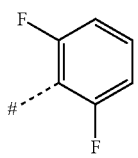 W⁴ wherein # denotes the point of attachment to the group $CR^{13}R^{14}$;
Z is oxygen;
n is zero or 1, in particular 1; and
among these, especially preferred are the isoxazoline compounds of the formulae II.1, II.2, II.3, II.4, II.5, II.6, II.7, II.8 and II.9

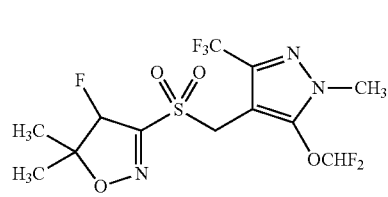 II.1

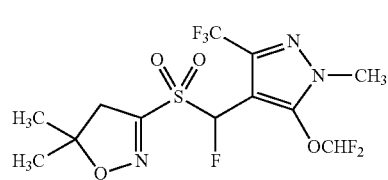 II.2

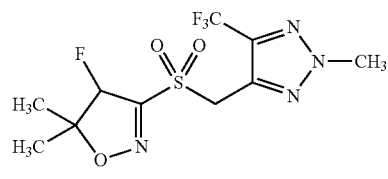 II.3

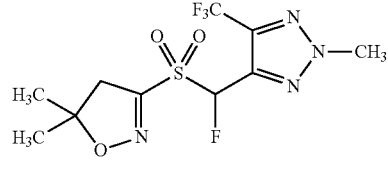 II.4

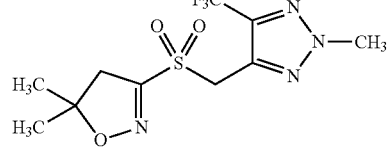 II.5

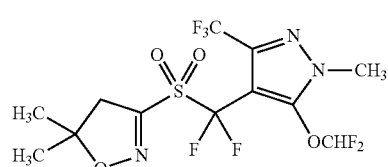 II.6

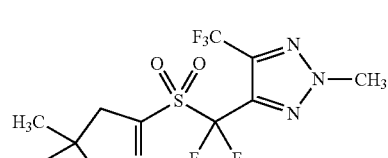 II.7

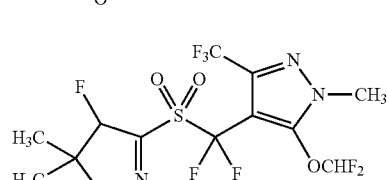 II.8

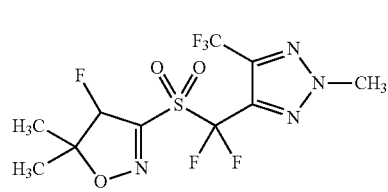 II.9 the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides;

c11) from the group of the cellulose biosynthesis inhibitors: chlorthiamid, dichlobenil, flupoxam, isoxaben, 1-Cyclohexyl-5-pentafluorphenyloxy-1⁴-[1,2,4,6]thiatriazin-3-ylamine and piperazine compounds of formula III,

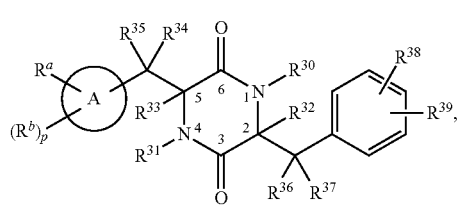

in which

A is phenyl or pyridyl where $R^a$ is attached in the ortho-position to the point of attachment of A to a carbon atom;

$R^a$ is CN, NO$_2$, $C_1$-$C_4$-alkyl, D-$C_3$-$C_6$-cycloalkyl, $C_1$-$C_4$-haloalkyl, $C_1$-$C_4$-alkoxy, $C_1$-$C_4$-haloalkoxy, O-D-$C_3$-$C_6$-cycloalkyl, S(O)$_q$R$^y$, $C_2$-$C_6$-alkenyl, D-$C_3$-$C_6$-cycloalkenyl, $C_3$-$C_6$-alkenyloxy, $C_2$-$C_6$-alkynyl, $C_3$-$C_6$-alkynyloxy, NR$^A$R$^B$, tri-$C_1$-$C_4$-alkylsilyl, D-C(=O)—R$^{a1}$, D-P(=O)(R$^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups R$^{aa}$ and/or R$^{a1}$, and, if $R^a$ is attached to a carbon atom, additionally halogen;

R$^y$ is $C_1$-$C_6$-alkyl, $C_3$-$C_4$-alkenyl, $C_3$-$C_4$-alkynyl, NR$^A$R$^B$ or $C_1$-$C_4$-haloalkyl and q is 0, 1 or 2;

R$^A$,R$^B$ independently of one another are hydrogen, $C_1$-$C_6$-alkyl, $C_3$-$C_6$-alkenyl and $C_3$-$C_3$-alkynyl; together with the nitrogen atom to which they are attached, R$^A$,R$^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups R$^{aa}$;

D is a covalent bond, $C_1$-$C_4$-alkylene, $C_2$-$C_6$-alkenyl or $C_2$-$C_6$-alkynyl;

R$^{a1}$ is hydrogen, OH, $C_1$-$C_8$-Alkyl, $C_1$-$C_4$-haloalkyl, $C_3$-$C_8$-cycloalkyl, $C_2$-$C_8$-alkenyl, $C_8$-$C_6$-cycloalkenyl, $C_2$-$C_8$-alkynyl, $C_1$-$C_6$-alkoxy, $C_1$-$C_4$-haloalkoxy, $C_3$-$C_8$-alkenyloxy, $C_3$-$C_8$-alkynyloxy, NR$^A$R$^B$, $C_1$-$C_6$-alkoxyamino, $C_1$-$C_6$-alkylsulfonylamino, $C_1$-$C_6$-alkylaminosulfonylamino, [di-($C_1$-$C_6$)alkylamino]sulfonylamino, $C_3$-$C_6$-alkenylamino, $C_3$-$C_6$-alkynylamino, N—($C_2$-$C_6$-alkenyl)-N—N—($C_2$-$C_6$-alkynyl)-N—($C_1$-$C_6$-alkyl)amino, N—($C_1$-$C_6$-alkoxy)-N—($C_1$-$C_6$-alkyl)amino, N—($C_2$-$C_6$-alkenyl)-N—($C_1$-$C_6$-alkoxy)amino, N—($C_2$-$C_6$-alkynyl)-N—($C_1$-$C_6$-alkoxy)-amino, $C_1$-$C_6$-alkylsulfonyl, tri-$C_1$-$C_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups R$^{aa}$;

R$^{aa}$ is halogen, OH, CN, NO$_2$, $C_1$-$C_4$-alkyl, $C_1$-$C_4$-haloalkyl, $C_1$-$C_4$-alkoxy, $C_1$-$C_4$-haloalkoxy, S(O)$_q$R$^y$, D-C(=O)—R$^{a1}$ and tri-$C_1$-$C_4$-alkylsilyl;

R$^b$ independently of one another are hydrogen, CN, NO$_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or S(O)$_q$R$^y$, R$^b$ together with the group R$^a$ or R$^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by R$^{aa}$;

p is 0, 1, 2 or 3;

R$^{30}$ is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, NR$^A$R$^B$, S(O)$_n$R$^y$, S(O)$_n$NR$^A$R$^B$, C(=O)R$^{40}$, CONR$^A$R$^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via D$^1$ and are unsubstituted or substituted by 1, 2, 3 or 4 groups R$^{aa}$, and also the following partially or fully R$^{aa}$-substituted groups: $C_1$-$C_4$-alkyl, $C_3$-$C_4$-alkenyl, $C_3$-$C_4$-alkynyl, $C_1$-$C_4$-alkoxy, $C_3$-$C_6$-cycloalkyl, $C_5$-$C_6$-cycloalkenyl, NR$^A$R$^B$, S(O)$_n$R$^y$, S(O)$_n$NR$^A$R$^B$, C(=O)R$^{25}$ and CONR$^A$R$^B$;

R$^{40}$ is hydrogen, $C_1$-$C_4$-alkyl, $C_1$-$C_4$-haloalkyl, $C_1$-$C_4$-alkoxy or $C_1$-$C_4$-haloalkoxy;

D$^1$ is carbonyl or a group D;

where in groups R$^{15}$, R$^a$ and their sub-substituents the carbon chains and/or the cyclic groups may carry 1, 2, 3 or 4 substituents R$^{aa}$ and/or R$^{a1}$;

R$^{31}$ is $C_1$-$C_4$-alkyl, $C_3$-$C_4$-alkenyl or $C_3$-$C_4$-alkynyl;

R$^{32}$ is OH, NH$_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-alkoxy-$C_1$-$C_4$-alkyl or C(=O)R$^{40}$;

R$^{33}$ is hydrogen, halogen, $C_1$-$C_4$-alkyl or $C_1$-$C_4$-haloalkyl, or R$^{33}$ and R$^{34}$ together are a covalent bond;

R$^{34}$, R$^{35}$, R$^{36}$, R$^{37}$ independently of one another are hydrogen, halogen, OH, CN, NO$_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

R$^{38}$, R$^{39}$ independently of one another are hydrogen, halogen, OH, haloalkyl, NR$^A$R$^B$, NR$^A$C(O)R$^{41}$, CN, NO$_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)R$^{41}$, phenoxy or benzyloxy, where in groups R$^{38}$ and R$^{39}$ the carbon chains and/or the cyclic groups may carry 1, 2, 3 or 4 substituents R$^{aa}$;

R$^{41}$ is $C_1$-$C_4$-alkyl or NR$^A$R$^B$;

among the piperazin compounds of formula III, preference is given to the piperazine compounds of the formula III, wherein A is phenyl or pyridyl where $R^a$ is attached in the ortho-position to the point of attachment of A to a carbon atom;

$R^a$ is CN, NO$_2$, $C_1$-$C_4$-alkyl, $C_1$-$C_4$-haloalkyl, $C_1$-$C_4$-alkoxy, $C_1$-$C_4$-haloalkoxy or D-C(=O)—R$^{a1}$;

R$^y$ is $C_1$-$C_6$-alkyl, $C_3$-$C_4$-alkenyl, $C_3$-$C_4$-alkynyl, NR$^A$R$^B$ or $C_1$-$C_4$-haloalkyl and q is 0, 1 or 2;

R$^A$,R$^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A, R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{30}$ is hydrogen, $C_1$-$C_{12}$-alkyl, $C_3$-$C_{12}$-alkenyl, $C_3$-$C_{12}$-alkynyl, $C_1$-$C_4$-alkoxy or C(=O)$R^{40}$, which can be partially or fully be substituted by $R^{aa}$ groups;

$R^{40}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{30}$, $R^a$ and their sub-substituents the carbon chains and/or the cyclic groups may carry 1, 2, 3 or 4 substituents $R^{aa}$ and/or $R^{a1}$;

$R^{31}$ is $C_1$-$C_4$-alkyl;

$R^{32}$ is OH, $NH_2$, $C_1$-$C_4$-alkyl, $C_3$-$C_6$-cycloalkyl, $C_1$-$C_4$-haloalkyl or C(=O)$R^{25}$;

$R^{33}$ is hydrogen, or $R^{33}$ and $R^{34}$ together are a covalent bond;

$R^{34}$, $R^{35}$, $R^{36}$, $R^{37}$ independently of one another are hydrogen;

$R^{38}$, $R^{39}$ independently of one another are hydrogen, halogen or OH;

c12) from the group of the decoupler herbicides:
dinoseb, dinoterb and DNOC and its salts;

c13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

c14) from the group of the auxin transport inhibitors:
diflufenzopyr, diflufenzopyr-sodium, naptalam and naptalam-sodium;

c15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flampprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Preferred herbicides C which can be used in combination with the anionic pesticide (preferably pesticide A1 (such as dicamba); or in another embodiment pesticide A2 (such as glyphosate)) are c1) from the group of the lipid biosynthesis inhibitors:
clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, benfuresate, dimepiperate, EPTC, esprocarb, ethofumesate, molinate, orbencarb, prosulfocarb, thiobencarb and triallate;

c2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl and tritosulfuron;

c3) from the group of the photosynthesis inhibitors:
ametryn, amicarbazone, atrazine, bentazone, bentazone-sodium, bromoxynil and its salts and esters, chloridazon, chlorotoluron, cyanazine, desmedipham, diquatdibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

c4) from the group of the protoporphyrinogen-IX oxidase inhibitors:
acifluorfen-sodium, bencarbazone, benzfendizone, butafenacil, carfentrazone-ethyl, cinidon-ethyl, flufenpyrethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5- dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydroisoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

c5) from the group of the bleacher herbicides:
aclonifen, beflubutamid, benzobicyclon, clomazone, diflufenican, fluorochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

c6) from the group of the EPSP synthase inhibitors:
glyphosate, glyphosate-isopropylammonium and glyphosate-trimesium (sulfosate);

c7) from the group of the glutamine synthase inhibitors:
glufosinate, glufosinate-P, glufosinate-ammonium;

c8) from the group of the DHP synthase inhibitors: asulam;

c9) from the group of the mitose inhibitors:
benfluralin, dithiopyr, ethalfluralin, oryzalin, pendimethalin, thiazopyr and trifluralin;

c10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

c11) from the group of the cellulose biosynthesis inhibitors:
dichlobenil, flupoxam, isoxaben, 1-Cyclohexyl-5-pentafluorphenyloxy-1$^4$-[1,2,4,6]thiatriazin-3-ylamine and the piperazine compounds of formula III as mentioned above;

c13) from the group of the auxin herbicides:
2,4-D and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluoroxypyr-meptyl, MCPA and its salts and esters, MCPB and its salts and esters, mecoprop-P and its salts and esters, picloram and its salts and esters, quinclorac, quinmerac, triclopyr and its salts and esters, and aminocyclopyrachlor and its salts and esters;

c14) from the group of the auxin transport inhibitors:
diflufenzopyr and diflufenzopyr-sodium;

c15) from the group of the other herbicides: bromobutide, cinmethylin, cumyluron, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam, tridiphane and 6-chloro-3-(2-cyclopropyl-6-methylphenoxy)-4-pyridazinol (CAS 499223-49-3) and its salts and esters.

Particularly preferred herbicides C which can be used in combination with the anionic pesticide (preferably pesticide A1 (such as dicamba); or in another embodiment pesticide A2 (such as glyphosate)) are:

c1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate;

c2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron;

c3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

c4) from the group of the protoporphyrinogen-IX oxidase inhibitors: flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

c5) from the group of the bleacher herbicides: clomazone, diflufenican, fluorochloridone, isoxaflutole, mesotrione, picolinafen, sulcotrione, tefuryltrione, tembotrione, topramezone, bicyclopyrone, amitrole and flumeturon;

c6) from the group of the EPSP synthase inhibitors: glyphosate, glyphosate-isopropylammonium and glyphosate-trimesium (sulfosate);

c7) from the group of the glutamine synthase inhibitors: glufosinate, glufosinate-P and glufosinate-ammonium;

c9) from the group of the mitose inhibitors: pendimethalin and trifluralin;

c10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

c11) from the group of the cellulose biosynthesis inhibitors: isoxaben and the piperazine compounds of formula III as mentioned above;

c13) from the group of the auxin herbicides: 2,4-D and its salts and esters, aminopyralid and its salts and its esters, clopyralid and its salts and esters, dicamba and its salts and esters, fluoroxypyr-meptyl, quinclorac, quinmerac and aminocyclopyrachlor and its salts and esters;

c14) from the group of the auxin transport inhibitors: diflufenzopyr and diflufenzopyr-sodium, c15) from the group of the other herbicides: dymron (=daimuron), indanofan, indaziflam, oxaziclomefone and triaziflam.

In another embodiment of the present invention the compositions according to the present invention comprise at least one anionic pesticide (preferably pesticide A1 (such as dicamba); or in another embodiment pesticide A2 (such as glyphosate)) and at least one safener C.

Safeners are chemical compounds which prevent or reduce damage on useful plants without having a major impact on the herbicidal action of the herbicidal active components of the present compostions towards unwanted plants. They can be applied either before sowings (e.g. on seed treatments, shoots or seedlings) or in the pre-emergence application or post-emergence application of the useful plant. The safeners and the anionic pesticide and/or the herbicides C can be applied simultaneously or in succession.

Examples of preferred safeners D are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

Especially preferred safeners D are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2, 5-trimethyl-3-(dichloroacetyl)-1,3-oxazolidine (R-29148, CAS 52836-31-4).

Particularly preferred safeners D are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane
(MON4660, CAS 71526-07-3) and 2,2,5-trimethyl-3-(dichloroacetyl)-1,3-oxazolidine (R-29148, CAS 52836-31-4).

The active compounds C of groups c1) to c15) and the active compounds D are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

If the herbicides C and/or the safeners D are capable of forming geometrical isomers, for example E/Z isomers, both the pure isomers and mixtures thereof may be used in the compositions according to the invention. If the herbicides C and/or the safeners D have one of more centers of chirality and are thus present as enantiomers or diastereomers, both the pure enantiomers and diastereomers and mixtures thereof may be used in the compositions according to the invention.

If the herbicides C and/or the safeners D have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Active compounds C and D having a carboxyl group can be employed in the form of the acid, in the form of an agriculturally suitable salt or else in the form of an agriculturally acceptable derivative in the compositions according to the invention, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl(1-methylhexyl) or isooctyl(2-ethylhexyl)esters. Preferred $C_1$-$C_4$-alkoxy-$C_1$-$C_4$-alkyl esters are the straight-chain or branched $C_1$-$C_4$-alkoxy ethyl esters, for example the methoxyethyl, ethoxyethyl or butoxyethyl ester. An example of a straight-chain or branched $C_1$-$C_{10}$-alkylthio ester is the ethylthio ester.

According to a preferred embodiment of the invention, the composition comprises as herbicidal active compound C or component B, at least one preferably exactly one herbicide B.

According to another preferred embodiment of the invention, the composition comprises as herbicidal active compound C or component B, at least two preferably exactly two herbicides C different from each other.

According to another preferred embodiment of the invention, the composition comprises as herbicidal active compound C or component B, at least three, preferably exactly three herbicides C different from each other.

According to another preferred embodiment of the invention, the composition comprises as safening component D at least one preferably exactly one safener C.

According to another preferred embodiment of the invention, the composition comprises as component B, at least one preferably exactly one herbicide B, and at lest one preferably exactly one safener C.

According to another preferred embodiment of the invention, the composition comprises as component B, preferably exactly two herbicides C different from each other, and at lest one, preferably exactly one, safener C.

According to another preferred embodiment of the invention, the composition comprises as component B, at least three, preferably exactly three herbicides C different from each other, and at lest one preferably exactly one safener C.

According to another preferred embodiment of the invention, the composition comprises as component A at least one, preferably exactly one, pesticide A1, and as component B, at least one preferably exactly one herbicide B.

According to another preferred embodiment of the invention, the composition comprises as component A at least one preferably exactly one pesticide A1, and as component B, at least two, preferably exactly two herbicides C different from each other.

According to another preferred embodiment of the invention, the composition comprises as component A at least one, preferably exactly one, pesticide A1, and as component B, at least three, preferably exactly three herbicides, C different from each other.

One preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

Another preferred embodiment of the invention relates to compositions according to the invention comprising, in addition to a pesticide A1, especially an active compound from the group consisting dicamba and 2,4-D (especially dicamba), at least one and especially exactly one herbicidally active compound from group c3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c4), in particular selected from the group consisting of flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydroisoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c5), in particular selected from the group consisting of clomazone, diflufenican, fluorochloridone, isoxaflutole, mesotrione, picolinafen, sulcotrione, tefuryltrione, tembotrione, topramezone, bicyclopyrone, amitrole and flumeturon.

Another preferred embodiment of the invention relates to compositions according to the invention comprising, in addition to a pesticide A1, especially an active compound from the group consisting of dicamba and 2A-D (especially dicamba), at least one and especially exactly one herbicidally active compound from group c6), in particular selected from the group consisting of glyphosate, glyphosate-isopropylammonium and glyphosate-trimesium (sulfosate).

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c7), in particular selected from the group consisting of glufosinate, glufosinate-P and glufosinate-ammonium.

Another preferred embodiment of the invention relates to compositions according to the invention comprising, in addition to a pesticide A1, especially an active compound from the group consisting of dicamba and 2A-D (especially dicamba), at least one and especially exactly one herbicidally active compound from group c9), in particular selected from the group consisting of pendimethalin and trifluralin.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a pesticide A1, especially an active compound from the group consisting of dicamba and 2,4-D (especially dicamba), at least one and especially exactly one herbicidally active compound from group c10), in particular selected from the group consisting of isoxazoline compounds of the formulae II.1, II.2, II.3, II.4, II.5, II.6, II.7, II.8 and II.9, as defined above.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c11), in particular isoxaben. Likewise, preference is given to compositions comprising in addition to a benzoxazinone of the formula I, preferably of formula I.a, especially an active compound from the group consisting of I.a.35, at least one and especially exactly one herbicidally active compound from group c10), in particular selected from the group consisting of piperazine compounds of formula III as defined above.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c13), in particular selected from the group consisting of 2,4-D and its salts and esters, aminopyralid and its salts such as aminopyralid-tris(2-hydroxypropyl) ammonium and its esters, clopyralid and its salts and esters, dicamba and its salts and esters, fluoroxypyr-meptyl, quinclorac, quinmerac and aminocyclopyrachlor and its salts and esters.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c14), in particular selected from the group consisting of diflufenzopyr and diflufenzopyr-sodium.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from group c15), in particular selected from the group consisting of dymron (=daimuron), indanofan, indaziflam, oxaziclomefone and triaziflam.

Another preferred embodiment of the invention relates to compositions according to the invention comprising, in addition to a pesticide A1, especially an active compound from the group consisting of dicamba and 2,4-D (especially dicamba), at least one and especially exactly one herbicidally active compound from the safeners C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

According to a further preferred embodiment of the invention, the composition comprises as component A at least one, preferably exactly one, pesticide A2, and as component B, at least one, preferably exactly one, herbicide B.

According to a further preferred embodiment of the invention, the composition comprises as component A at least one, preferably exactly one, pesticide A2, and as component B, at least two, preferably exactly two, herbicides C different from each other.

According to a further preferred embodiment of the invention, the composition comprises as component A at least one, preferably exactly one, pesticide A2, and as component B, at least three, preferably exactly three herbicides, C different from each other.

Another preferred embodiment of the invention relates to compositions according to the invention comprising, in addition to a pesticide A2, especially an active compound from the group consisting of glyphosate, at least one and especially exactly one herbicidally active compound from group c1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

Another preferred embodiment of the invention relates to compositions according to the invention comprising, in addition to a pesticide A2, especially an active compound from the group consisting of glyphosate, at least one and especially exactly one herbicidally active compound from group c2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

Another preferred embodiment of the invention relates to compositions according to the invention comprising, in addition to a pesticide A2, especially an active compound from the group consisting glyphosate, at least one and especially exactly one herbicidally active compound from group c3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

Another preferred embodiment of the invention relates to compositions according to the invention comprising, in addition to a pesticide A2, especially an active compound from the group consisting of glyphosate, at least one and especially exactly one herbicidally active compound from group c4), in particular selected from the group consisting of flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione.

Another preferred embodiment of the invention relates to compositions according to the invention comprising, in addition to a pesticide A2, especially an active compound from the group consisting of glyphosate, at least one and especially exactly one herbicidally active compound from group c5), in particular selected from the group consisting of clomazone, diflufenican, fluorochloridone, isoxaflutole, mesotrione, picolinafen, sulcotrione, tefuryltrione, tembotrione, topramezone, bicyclopyrone, amitrole and flumeturon.

Another preferred embodiment of the invention relates to compositions according to the invention comprising, in addition to a pesticide A2, especially an active compound from the group consisting of glyphosate, at least one and especially exactly one herbicidally active compound from group c6), in particular selected from the group consisting of glyphosate, glyphosate-isopropylammonium and glyphosate-trimesium (sulfosate).

Another preferred embodiment of the invention relates to compositions according to the invention comprising, in addition to a pesticide A2, especially an active compound from the group consisting of glyphosate, at least one and especially exactly one herbicidally active compound from group c7), in particular selected from the group consisting of glufosinate, glufosinate-P and glufosinate-ammonium.

Another preferred embodiment of the invention relates to compositions according to the invention comprising, in addition to a pesticide A2, especially an active compound from the group consisting of glyphosate, at least one and especially exactly one herbicidally active compound from group c9), in particular selected from the group consisting of pendimethalin and trifluralin.

Another preferred embodiment of the invention relates to compositions according to the invention comprising, in addition to a pesticide A2, especially an active compound from the group consisting of glyphosate, at least one and especially exactly one herbicidally active compound from group c10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a pesticide A2, especially an active compound from the group consisting of glyphosate, at least one and especially exactly one herbicidally active compound from group c10), in particular selected from the group consisting of isoxazoline compounds of the formulae II.1, II.2, II.3, II.4, II.5, II.6, II.7, II.8 and II.9, as defined above.

Another preferred embodiment of the invention relates to compositions according to the invention comprising, in addition to a pesticide A2, especially an active compound from the group consisting of glyphosate, at least one and especially exactly one herbicidally active compound from group c11), in particular isoxaben. Likewise, preference is given to compositions comprising in addition to a benzoxazinone of the formula I, preferably of formula I.a, especially an active compound from the group consisting of I.a.35, at least one and especially exactly one herbicidally active compound from group c10), in particular selected from the group consisting of piperazine compounds of formula III as defined above.

Another preferred embodiment of the invention relates to compositions according to the invention comprising, in addition to a pesticide A2, especially an active compound from the group consisting of glyphosate, at least one and especially exactly one herbicidally active compound from group c13), in particular selected from the group consisting of 2,4-D and its salts and esters, aminopyralid and its salts such as aminopyralid-tris(2-hydroxypropyl)ammonium and its esters, clopyralid and its salts and esters, dicamba and its salts and esters, fluoroxypyr-meptyl, quinclorac, quinmerac and aminocyclopyrachlor and its salts and esters.

Another preferred embodiment of the invention relates to compositions according to the invention comprising, in addition to a pesticide A2, especially an active compound from the group consisting of glyphosate, at least one and especially exactly one herbicidally active compound from group c14), in particular selected from the group consisting of diflufenzopyr and diflufenzopyr-sodium.

Another preferred embodiment of the invention relates to compositions according to the invention comprising, in addition to a pesticide A2, especially an active compound from the group consisting of glyphosate, at least one and especially exactly one herbicidally active compound from group c15), in particular selected from the group consisting of dymron (=daimuron), indanofan, indaziflam, oxaziclomefone and triaziflam.

Another preferred embodiment of the invention relates to compositions according to the invention comprising, in addition to a pesticide A2, especially an active compound from the group consisting of glyphosate, at least one and especially exactly one herbicidally active compound from the safeners C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Further preferred embodiments relate to ternary compositions which correspond to the binary compositions as mentioned above and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, anionic pesticides and either one or more, for example 1, 2 or 3, herbicides C or one or more safeners. Correspondingly, the term "ternary compositions" includes compositions comprising one or more, for example 1, 2 or 3, active compounds of the formula I, one or more, for example 1, 2 or 3, herbicides C and one or more, for example 1, 2 or 3, safeners C.

In binary compositions comprising at least one anionic pesticide as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one anionic pesticide as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one anionic pesticide as component A, at least one herbicide C and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+C to component D is preferably in the range of from 1:500 to 500:1, in particular in the range of from 1:250 to 250:1 and particularly preferably in the range of from 1:75 to 75:1.

The compositions according to the invention are suitable as herbicides. They are suitable as such or as an appropriately formulated composition. The compositions according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

Depending on the application method in question, the compositions according to the invention can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Brassica juncea, Brassica campestris, Camellia sinensis, Carthamus tinctorius, Carya illinoinensis, Citrus limon, Citrus sinensis, Coffea arabica (Coffea canephora, Coffea liberica), Cucumis sativus, Cyn-* odon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pistacia vera, Pisum sativum, Prunus avium, Prunus persica, Pyrus communis, Prunus armeniaca, Prunus cerasus, Prunus dulcis and prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera, Zea mays.

Preferred crops are: Arachis hypogaea, Beta vulgaris spec. altissima, Brassica napus var. napus, Brassica oleracea, Brassica juncea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus spec., Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera and Zea mays The compositions according to the invention can also be used in genetically modified plants, e.g. to alter their traits or characteristics. The term "genetically modified plants" is to be understood as plants, which genetic material has been modified by the use of recombinant DNA techniques in a way that under natural circumstances it cannot readily be obtained by cross breeding, mutations, natural recombination, breeding, mutagenesis, or genetic engineering. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, are particularly useful with the compositions according to the invention. Tolerance to classes of herbicides has been developed such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase (PPO) inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors.

These herbicide resistance technologies are for example, described in Pest Management Science 61, 2005, 246; 61, 2005, 258; 61, 2005, 277; 61, 2005, 269; 61, 2005, 286; 64, 2008, 326; 64, 2008; 332 Weed Science 57, 2009, 108; Australian Journal of Agricultural Research 58, 2007, 708; Science 316, 2007, 1185; and references quoted therein. Examples of these herbicide resistance technologies are also described in US 2008/0028482, US2009/0029891, WO 2007/143690, WO 2010/080829, U.S. Pat. Nos. 6,307,129, 7,022,896, US 2008/0015110, U.S. Pat. Nos. 7,632,985, 7,105,724, and 7,381,861, each herein incorporated by reference.

Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate, dicamba, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozyme (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Furthermore, it has been found that the compositions according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the compositions according to the invention.

As desiccants, the compositions according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval in which the individual cotton plants mature leads to an increased fiber quality after harvesting.

The compositions according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

The herbicidal compositions according to the present invention can be applied pre- or post-emergence, or together with the seed of a crop plant. It is also possible to apply the compounds and compositions by applying seed, pretreated with a composition of the invention, of a crop plant. If the active compounds A and C and if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the composition according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula I according to the invention or the compositions prepared therefrom. Here, the herbicidal compositions can be applied diluted or undiluted.

The term seed comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the active compound are from 0.0001 to 3.0, preferably 0.01 to 1.0 kg/ha of active substance (a.s.), depending on the control target, the season, the target plants and the growth stage. To treat the seed, the compounds I are generally employed in amounts of from 0.001 to 10 kg per 100 kg of seed.

Moreover, it may be advantageous to apply the compositions of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

The salts according to the invention can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention. Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF). Usually the composition types (e.g. SC, OD, FS, EC, WG, SG, WP, SP, SS, WS, GF) are employed diluted. Composition types such as DP, DS, GR, FG, GG and MG are usually used undiluted. The compositions are prepared in a known manner. When the agrochemical composition is an aqueous composition, the salt according to the invention may dissociate into anions and cations.

The agrochemical compositions may also comprise auxiliaries which are customary in agrochemical compositions. The auxiliaries used depend on the particular application form and active substance, respectively. Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols (such as ethylene glycol or 1,2-propylene glycol), ketones such as cyclohexanone and gamma-butyrolactone, fatty acid dimethylamides, fatty acids and fatty acid esters and strongly polar solvents, e.g. amines such as N-methylpyrrolidone. Preferred solvent is water.

Solid carriers are mineral earths such as silicates, silica gels, talc, kaolins, limestone, lime, chalk, bole, loess, clays, dolomite, diatomaceous earth, calcium sulfate, magnesium sulfate, iron sulfate, magnesium oxide, ground synthetic materials, fertilizers, such as e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, welters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof. Further suitable surfactants (especially for agrochemical compositions comprising glyphosate) are alkoxylated $C_{4-22}$-alkylamines, such as ethoxylated tallow amine (POEA) and the surfactans disclosed in EP1389040 (e.g. those in Examples 1 to 14).

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidons, polyvinylacetates, polyvinyl alcohols and cellulose ethers (Tylose®, Shin-Etsu, Japan). Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange range 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Powders, materials for spreading and dusts can be prepared by mixing or concomitantly grinding the salts according to the invention and, if appropriate, further active substances, with at least one solid carrier. Granules, e.g. coated granules, impregnated granules and homogeneous granules, can be prepared by binding the active substances to solid carriers Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:

1. Composition Types for Dilution with Water i) Water-Soluble Concentrates (SL, LS)

10 parts by weight of a salt according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible Concentrates (DC)

20 parts by weight of a salt according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of a salt according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of a salt according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of a salt according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of a salt according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of a salt according to the invention are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of a salt according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of a salt according to the invention are ground finely and mixed intimately with 95 parts by weight of finely divided kaolin. This gives a dustable composition having an active substance content of 5% by weight.

x) Granules (GR, FG, GG, MG)

0.5 parts by weight of a salt according to the invention is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of a salt according to the invention are dissolved in 90 parts by weight of an organic solvent, e.g. xylene. This gives a composition to be applied undiluted having an active substance content of 10% by weight.

The composition types i), iv), vii) and x) are preferred. The composition type i) is especially preferred.

The agrochemical compositions generally comprise between 0.01 and 95%, preferably between 0.1 and 90%, most preferably between 0.5 and 90%, by weight of salts according to the invention. These active substances are employed in a purity of from 90% to 100%, preferably from 95% to 100% (according to NMR spectrum). Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations.

Very suitable agrochemical compositions of the salts according to the invention are:

a) Water-Soluble Concentrate
  10-70 wt % salt according to the invention and optionally at least one further pesticide, 30-90 wt % water, and optionally up to 10 wt % auxiliaries, such as surfactants, thickeners, or colorants, wherein the amount of all components adds up to 100 wt %.

b) Wettable-Powder
  10-90 wt % salt according to the invention and optionally at least one further pesticide, 9-80 wt % solid carrier, 1-10 wt % surfactant, and optionally auxiliaries, wherein the amount of all components adds up to 100 wt %.

c) Water Dispersable Granules
  10-90 wt % salt according to the invention and optionally at least one further pesticide, 9-80 wt % solid carrier, 1-10 wt % surfactant, and optionally auxiliaries, wherein the amount of all components adds up to 100 wt %.

d) Granules
  0.5-20 wt % salt according to the invention and optionally at least one further pesticide, 0.5-20 wt % solvent, 40-99 wt % solid carrier, and optionally auxiliaries, wherein the amount of all components adds up to 100 wt %.

Especially suitable agrochemical compositions of the salts according to the invention are:

a) Water-Soluble Concentrate
  20-60 wt % salt comprising dicamba and (B1), dicamba and (B2), dicamba and (B3), or dicamba and (B4) [preferably a salt comprising dicamba and (B1.1), dicamba and (B1.2), dicamba and (B1.3), dicamba and (B1.4), dicamba and (B1.5), dicamba and (B1.6), dicamba and (B1.7), dicamba and (B1.8), dicamba and (B1.9), dicamba and (B1.10), dicamba and (B1.11), or dicamba and (B1.12)] and optionally at least one further pesticide, 40-80 wt % water, and optionally up to 10 wt % auxiliaries, such as surfactants, thickeners or colorants, wherein the amount of all components adds up to 100 wt %.)

b) Wettable-Powder 0-90 wt % salt comprising dicamba and (B1), dicamba and (B2), dicamba and (B3), or dicamba and (B4) [preferably a salt comprising dicamba and (B1.1), dicamba and (B1.2), dicamba and (B1.3), dicamba and (B1.4), dicamba and (B1.5), dicamba and (B1.6), dicamba and (B1.7), dicamba and (B1.8), dicamba and (B1.9), dicamba and (B1.10), dicamba and (B1.11), or dicamba and (B1.12)] and optionally at least one further pesticide, 9-80 wt % solid carrier, 1-10 wt % surfactant, and optionally auxiliaries, wherein the amount of all components adds up to 100 wt %.)

c) Water Dispersable Granules 10-90 wt % salt comprising dicamba and (B1), dicamba and (B2), dicamba and (B3), or dicamba and (B4) [preferably a salt comprising dicamba and (B1.1), dicamba and (B1.2), dicamba and (B1.3), dicamba and (B1.4), dicamba and (B1.5), dicamba and (B1.6), dicamba and (B1.7), dicamba and (B1.8), dicamba and (B1.9), dicamba and (B1.10), dicamba and (B1.11), or dicamba and (B1.12)] and optionally at least one further pesticide, 9-80 wt % solid carrier, 1-10 wt % surfactant, and optionally auxiliaries, wherein the amount of all components adds up to 100 wt %.

d) Granules 0.5-20 wt % salt comprising dicamba and (B1), dicamba and (B2), dicamba and (B3), or dicamba and (B4) [preferably a salt comprising dicamba and (B1.1), dicamba and (B1.2), dicamba and (B1.3), dicamba and (B1.4), dicamba and (B1.5), dicamba and (B1.6), dicamba and (B1.7), dicamba and (B1.8), dicamba and (B1.9), dicamba and (B1.10), dicamba and (B1.11), or dicamba and (B1.12)] and optionally at least one further pesticide, 0.5-20 wt % solvent (e.g. glycols), 40-99 wt % solid carrier, and optionally auxiliaries, wherein the amount of all components adds up to 100 wt %.

In another embodiment the especially suitable agrochemical compositions of the salts according to the invention are:

a) Water-Soluble Concentrate 20-60 wt % salt comprising glyphosate and (B1.2), glyphosate and (B1.5), or glyphosate and (B3) [preferably salt comprising glyphosate and (B1.1), glyphosate and (B1.5), glyphosate and (B1.10) glyphosate and (B1.11), or glyphosate and (B1.12)] and optionally at least one further pesticide, 80-40 wt % water, and optionally up to 10 wt % auxiliaries, such as surfactants (e.g. ethoxylated tallow amine), thickeners or colorants, wherein the amount of all components adds up to 100 wt %.

b) Wettable-Powder 10-90 wt % salt comprising glyphosate and (B1.2), glyphosate and (B1.5), or glyphosate and (B3) [preferably salt comprising glyphosate and (B1.1), glyphosate and (B1.5), glyphosate and (B1.10), glyphosate and (B1.11), or glyphosate and (B1.12)] and optionally at least one further pesticide, 9-80 wt % solid carrier, 1-10 wt % surfactant (e.g. ethoxylated tallow amine), and optionally auxiliaries, wherein the amount of all components adds up to 100 wt %.

c) Water Dispersable Granules 10-90 wt % salt comprising glyphosate and (B1.2), glyphosate and (B1.5), or glyphosate and (B3) [preferably salt comprising glyphosate and (B1.1), glyphosate and (B1.5), glyphosate and (B1.10), glyphosate and (B1.11), or glyphosate and (B1.12)] and optionally at least one further pesticide, 9-80 wt % solid carrier, 1-10 wt % surfactant (e.g. ethoxylated tallow amine), and optionally auxiliaries, wherein the amount of all components adds up to 100 wt %.)

d) Granules 0.5-20 wt % salt comprising glyphosate and (B1.2), glyphosate and (B1.5), or glyphosate and (B3) [preferably salt comprising glyphosate and (B1.1), glyphosate and (B1.5), glyphosate and (B1.10), glyphosate and (B1.11), or glyphosate and (B1.12)] and optionally at least one, further pesticide, 0.5-20 wt % solvent (e.g. glycols), 40-99 wt % solid carrier, and optionally auxiliaries (e.g. ethoxylated tallow amine), wherein the amount of all components adds up to 100 wt %.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), diflufenzopyr as further pesticide and optionally an adjuvant. This agrochemical composition may in another embodiment, comprise additionally a safener (preferably isoxafiden-ethyl).

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), atrazine as further pesticide and optionally an adjuvant. This agrochemical composition may, in another embodiment, be present in form of suspension concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), an imidazolinone herbicide as further pesticide and optionally an adjuvant. This agrochemical composition may in another embodiment, be present in form of water-soluble concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), pyraclostrobin as further pesticide and optionally an adjuvant. This agrochemical composition may in another embodiment, be present in form of suspension concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), pyraclostrobin and glyphosate as further pesticide and optionally an adjuvant. This agrochemical composition may, in another embodiment, be present in form of a suspension concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), naptalam as further pesticide and optionally an adjuvant. This agrochemical composition may in another embodiment, be present in form of water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), quinclorac as further pesticide and optionally an adjuvant. This agrochemical composition may, in another embodiment, be present in form of water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), saflufenacil as further pesticide and optionally an adjuvant. This agrochemical composition may in another embodiment, be present in form of a suspension concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), glufosinate as further pesticide and optionally an adjuvant. This agrochemical composition may, in another embodiment, be present in form of a water-soluble concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), pyroxasulfon as further pesticide and optionally an adjuvant. This agrochemical composition may, in another embodiment, be present in form of a suspension concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), cloquintocet as further pesticide and optionally an adjuvant.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), MCPA as further pesticide and optionally an adjuvant. This agrochemical composition may, in another embodiment, be present in form of a water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), 2,4-D as further pesticide and optionally an adjuvant. This agrochemical composition may in another embodiment, be present in form of a water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), 2,4-D and MCPA as further pesticide and optionally an adjuvant. This agrochemical composition may, in another embodiment, be present in form of a water-soluble concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), MCPP and MCPA as further pesticide and optionally an adjuvant. This agrochemical composition may, in another embodiment, be present in form of a water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), MCPP and 2,4-D as further pesticide and optionally an adjuvant. This agrochemical composition may, in another embodiment, be present in form of a water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), bentazone as further pesticide and optionally an adjuvant. This agrochemical composition may, in another embodiment, be present in form of a water-soluble concentrate. This agrochemical composition may, in another embodiment, be present in form of a soluble granule.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), tritosulfuron as further pesticide and optionally an adjuvant.

In a further especially preferred embodiment, the agrochemical composition is a emulsion in water, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), DMTA as further pesticide and optionally an adjuvant. This agrochemical composition may, in another embodiment, comprise additionally an imidazolinone herbicide as further pesticide.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), nicosulfuron as further pesticide and optionally an adjuvant.

In a further especially preferred embodiment, the agrochemical composition is an emulsion in water, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), pendimethalin as further pesticide and optionally an adjuvant.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8) (B1.9), (B1.10), (B1.11), or (B1.12), topramezone as further pesticide and optionally an adjuvant. This agrochemical composition may in another embodiment, be present in form of a water-soluble concentrate. This agrochemical composition may in another embodiment, be present in form of a soluble granule.

In a further especially preferred embodiment, the agrochemical composition is an emulsion in water, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), aminocyclopyrachlor as further pesticide and optionally an adjuvant. This agrochemical composition may, in another embodiment, be present in form of a emulsion concentrate.

In a further especially preferred embodiment, the agrochemical composition is a water-dispersible granule, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), aminopyralid as further pesticide and optionally an adjuvant. This agrochemical composition may, in another embodiment, be present in form of a water-soluble concentrate.

In a further especially preferred embodiment, the agrochemical composition is an emulsion in water, which comprises a salt of dicamba and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), triclopyr as further pesticide and optionally an adjuvant. This agrochemical composition may, in another embodiment, be present in form of a emulsion concentrate.

In a further especially preferred embodiment, the agrochemical composition is a water-dispersible granule, which comprises a salt of glyphosate and a cationic polyamine selected from (B1.1), (B1.2), (B1.3), (B1.4), (B1.5), (B1.6), (B1.7), (B1.8), (B1.8), (B1.9), (B1.10), (B1.11), or (B1.12), pyraclostrobin as further pesticide and optionally an adjuvant. This agrochemical composition may, in another embodiment, be present in form of a suspension concentrate.

The salts according to the invention are also very useful to substitute the pesticide in known agrochemical compositions. For example, the salt comprising dicamba as anionic pesticide and a cationic polyamine of the formula (B1) or (B2) (preferably (B1.1), (B1.2), (B1.3), (B1.4), (B1.5), (B1.6), (B1.7), (B1.8), (B1.8), (B1.9), (B1.10), (B1.11), or (B1.12)) may substitute known dicamba salts, such as dicamba sodium, dicamba dimethylamine, dicamba diglycolamine, in the commercial products like BANVEL®+2,4-D, BANVEL HERBICIDE®, BANVEL-K+ATRAZINE®, BRUSHMASTER®, CELEBRITY PLUS®, CIMARRON MAX®, CLARITY HERBICIDE®, COOL POWER®, DIABLO HERBICIDE®, DICAMBA DMA SALT, DISTINCT HERBICIDE®, ENDRUN®, HORSEPOWER*®, LATIGO®, MARKSMAN HERBICIDE®, MACAMINE-D®, NORTHSTAR HERBICIDE®, OUTLAW HERBICIDE®, POWER ZONE®, PROKOZ VESSEL®, PULSAR®, Q4 TURF HERBICIDE®, RANGESTAR®, REQUIRE Q®, RIFLE®, RIFLE PLUS®, RIFLE-D®, SPEED ZONE®, STATUS HERBICIDE®, STERLING BLUE®, STRUT®, SUPER TRIMEC*®, SURGE*®, TRIMEC BENTGRASS*®, TRIMEC CLASSIC*®, TRIMEC PLUS*®, TRIPLET SF®, TROOPER EXTRA®, VANQUISH®, VETERAN 720®, VISION HERBICIDE®, WEEDMASTER®, YUKON HERBICIDE®.

Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting. In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The salts according to the invention can also be present together with other active substances, e.g. with herbicides, insecticides, growth regulators, fungicides or else with fertilizers, as pre-mix or if appropriate, not until immediately prior to use (tank mix).

The present invention also relates to a method of combating harmful insects and/or phytopathogenic fungi, which comprises contacting plants, seed, soil or habitat of plants in or on which the harmful insects and/or phytopathogenic fungi are growing or may grow, plants, seed or soil to be protected from attack or infestation by said harmful insects and/or phytopathogenic fungi with an effective amount of the agrochemical formulation according to the invention. The anionic pesticides comprises usually an insecticide and/or an fungicide. For example, for combating harmful insects the agrochemical formulation comprises an insecticide. For example, for combating phytopathogenic fungi the agrochemical formulation comprises a fungicide.

The present invention further relates to a method of controlling undesired vegetation, which comprises allowing a herbicidal effective amount of the agrochemical formulation according to the invention to act on plants, their habitat or on seed of said plants. In a preferred embodiment, the method may also include plants that have been rendered tolerant to the application of the agrochemical formulation wherein the anionic pesticide is a herbicide. The methods generally involve applying an effective amount of the agrochemical formulation of the invention comprising a selected herbicide to a cultivated area or crop field containing one or more crop plants which are tolerant to the herbicide. Although any undesired vegetation may be controlled by such methods, in some embodiments, the methods may involve first identifying undesired vegetation in an area or field as susceptible to the selected herbicide. Methods are provided for controlling the undesired vegetation in an area of cultivation, preventing the development or the appearance of undesired vegetation in an area of cultivation, producing a crop, and increasing crop safety. Undesired vegetation, in the broadest sense, is understood as meaning all those plants which grow in locations where they are undesired, which include but is not limited to plant species generally regarded as weeds.

In addition, undesired vegetation can also include undesired crop plants that are growing in an identified location. For example, a volunteer maize plant that is in a field that predominantly comprises soybean plants can be considered undesirable. Undesired plants that can be controlled by the methods of the present invention include those plants that were previously planted in a particular field in a previous season, or have been planted in an adjacent area and include crop plants including soybean, corn, canola, cotton, sunflowers, and the like. In some aspects, the crop plants can be tolerant of herbicides, such as glyphosate, ALS-inhibitors, or glufosinate herbicides. The methods comprise planting the area of cultivation with crop plants which are tolerant to the herbicide, and in some embodiments, applying to the crop, seed, weed, undesired plant, soil, or area of cultivation thereof an effective amount of an herbicide of interest. The herbicide can be applied at any time during the cultivation of the tolerant plants. The herbicide can be applied before or after the crop is planted in the area of cultivation. Also provided are methods of controlling glyphosate tolerant weeds or crop plants in a cultivated area comprising applying an effective amount of herbicide other than glyphosate to a cultivated area having one or more plants that are tolerant to the other herbicide.

The term "herbicidal effective amount" denotes an amount of pesticidal active component, such as the salt or the further pesticide, which is sufficient for controlling undesired vegetation and which does not result in a substantial damage to the treated plants. Such an amount can vary in a broad range and is dependent on various factors, such as the species to be controlled, the treated cultivated plant or material, the climatic conditions and the specific pesticidal active component used.

The term "controlling weeds" refers to one or more of inhibiting the growth, germination, reproduction, and/or proliferation of; and/or killing, removing, destroying, or otherwise diminishing the occurrence and/or activity of a weed and/or undesired plant.

The salts and the agrochemical formulation according to the invention have excellent herbicidal activity against a broad spectrum of economically important monocotyledonous and dicotyledonous harmful plants, such as broad-leaved weeds, weed grasses or Cyperaceae. The active compounds also act efficiently on perennial weeds which produce shoots from rhizomes, root stocks and other perennial organs and which are difficult to control. Specific examples may be mentioned of some representatives of the monocotyledonous and dicotyledonous weed flora which can be controlled by the compounds according to the invention, without the enumeration being restricted to certain species. Examples of weed species on which the herbicidal compositions act efficiently are from amongst the monocotyledonous weed species, *Avena* spp., *Alopecurus* spp., *Apera* spp., *Brachiaria* spp., *Bromus* spp., *Digitaria* spp., *Lolium* spp., *Echinochloa* spp., *Leptochloa* spp., *Fimbristylis* spp., *Panicum* spp., *Phalaris* spp., *Poa* spp., *Setaria* spp. and also *Cyperus* species from the annual group, and among the perennial species, *Agropyron, Cynodon, Imperata* and *Sorghum* and also perennial *Cyperus* species. In the case of the dicotyledonous weed species, the spectrum of action extends to genera such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. *Eclipta* spp., *Sesbania* spp., *Aeschynomene* spp. and *Viola* spp., *Xanthium* spp. among the annuals, and *Convolvulus, Cirsium, Rumex* and *Artemisia* in the case of the perennial weeds.

The present invention further relates to seed comprising the salt according to the invention. Preferably, the seed is coated with an agrochemical formulation comprising the salt according to the invention.

The present invention offers various advantages: The salts according to the invention show a low volatility. The volatility was also reduced compared to commercially available salts or the commercially free acids of the corresponding pesticides. For example, the amine salts of dicamba according to the invention have a lower volatility compared to dicamba free acid (present in Vision®) or to dicamba dimethylamine salt (present in Banvel®). Further on, the salts according to the invention are easily prepared starting from cheap, industrially available compounds, which are easy to handle. The pesticidal activity remains at a level equivalent to known salts or the free acid of the pesticide. The salts have a high solubility in water.

The invention is further illustrated but not limited by the following examples.

EXAMPLES

Dicamba acid: A technical quality of the herbicide comprising 90 wt % dicamba free acid.
2,4-D acid: A technical quality of the herbicide comprising 98 wt % 2,4-D in its free acid form.

Jeffcat® Z-130: N'-(3-(dimethylamino)propyl)-N,N-dimethyl-1,3-propanediamine (Bp 222° C.), commercially available from Huntsman, USA.

Jeffcat® ZR-40: N,N,N',N'',N''-pentamethyl-dipropylenetriamine (Bp 227° C.), commercially available from Huntsman, USA.

Tetraethylenepentamine (TEPA): A technical quality (Bp 288° C. extrapolated with decomposition; Bp 215° C. at 50 mm Hg) comprising linear TEPA, aminoethyltris-aminoethylamine (AE-IAEA), aminoethyldiaminoethylpiperazine (AE-DAEP) and aminoethylpiperazinoethylethylenediamine (AE-PEEDA); commercially available from Dow Chemical Company.

Banvel®: Agrochemical formulation of dicamba salt of dimethylamine (watersoluble concentrate SL, 480 g/l, commercially available from Syngenta).

Clarity®: Agrochemical formulation of dicamba salt of 2-(-aminoethoxy)ethanol (watersoluble concentrate SL, 480 g/l, commercially available from BASF Cooperation).

Vision®: Agrochemical formulation of dicamba free acid (watersoluble concentrate SL, 450 g/l, commercially available from Helena Corp., USA).

Example 1

Preparation of Salts

Salts were prepared comprising dicamba or 2,4-D as pesticide anion and various polyamine cations. A known quantity of dicamba acid or 2,4-D acid were suspended in water while stirring. The suspension was titrated with polyamine to a pH of 7.0 to 8.0 until all solids were dissolved and the salts have formed. Additional water was added to adjust the desired concentration of dicamba (480 g/l) or 2,4-D (250 g/l). Table 1 and 2 list the details of the final compositions. The dicamba concentration was 44.4 wt % in each case, and the 2,4-D concentration was 21.1 wt %. The water concentration added up to 100 wt % in each case. The quality of the polyamine is given in parenthesis. It was demonstrated, that all tested salts have a very good solubility in water, i.e. that dicamba salts are soluble up to at least 480 g/l and 2,4-D salts are soluble up to at least 250 g/l.

TABLE 1

Dicamba salts

| Entry | Type of polyamine cation | Concentration (w/w %) |
| --- | --- | --- |
| 1 | Isophorone diamine (99.7%) | 16.7 |
| 2 | Aminoethylethanolamine (99.9%) | 14.3 |
| 3 | Aminoethylpiperazine (98.8%) | 12.7 |
| 4 | Jeffcat ® Z-130 (99.5%) | 15.0 |
| 5 | Diethylenetriamine (98%) | 10.3 |
| 6 | Tetraethylenepentamine (98%) | 13.3 |
| 7 | N,N-Bis(3-aminopropyl)-methylamine (100%) | 11.5 |
| 8 | Jeffcat ® ZR-40 (99.1%) | 16.0 |

TABLE 2

2,4-D salts

| Entry | Type of polyamine cation | Concentration (w/w %) |
| --- | --- | --- |
| 1 | Aminoethylethanolamine (99.9%) | 7.1 |
| 2 | Jeffcat ® Z-130 (99.5%) | 6.8 |
| 3 | Diethylenetriamine (98%) | 5.0 |
| 4 | Tetraethylenepentamine (98%) | 6.3 |

Example 2

Volatility Determined by TGA of Dicamba Salts and 2,4-D Salts

The volatility of the aqueous solutions of dicamba (480 g/l) or 2,4-D (250 g/l) as prepared in Example 1 was determined by analyzing the wt % loss per minute as calculated by the slope between 400 min and 1200 min of a TGA (thermal gravimetric analysis) analysis. The measurement conditions on a TA Instrument TGA Q50 were as follows: Pan type: Platinum; sample size 25 µl leveling uniformly on pan surface, balance purge flow 40 ml/min; sample purge flow 60 ml/min; temperature procedure: Start at 20° C., ramp 10° C./min to 100° C., then isothermal for 1200 min. The results of the volatility (as wt % loss per min) are summarized in table 3 and 4. Thus it was demonstrated, that the salts of dicamba or 2,4-D according to the invention had a reduced volatility compared to commercial dicamba salt formulations.

The aminopropylmorpholine (APM) salt of dicamba is known from EP 0 375 624. However, this salt has a lower solubility compared to the polyamine salts of the invention. It was not possible to prepare an aqueous solution with a concentration of higher than 300 g/l. The volatility of this solution was 0.0021 wt % loss per min, but was expected to be higher for a concentration of 480 g/l.

TABLE 3

Dicamba salts

| Entry | Type of polyamine cation | Volatility (wt % loss per min) | Volatility (normalized) |
| --- | --- | --- | --- |
| 1 | — (Dicamba acid)[a] | 0.060 | 100.0 |
| 2 | Dimethylamine[a] | 0.011 | 17.8 |
| 3 | 2-(-Aminoethoxy)ethanol[a] | 0.0032 | 5.4 |
| 4 | Isophorone diamine (99.7%) | 0.0002 | 0.4 |
| 5 | Aminoethylethanolamine (99.9%) | 0.0018 | 3.1 |
| 6 | Aminoethylpiperazine (98.8%) | 0.0002 | 0.4 |
| 7 | Jeffcat ® Z-130 (99.5%) | 0.0017 | 2.9 |
| 8 | Diethylenetriamine (98%) | 0.0004 | 0.7 |
| 9 | Tetraethylenepentamine (98%) | 0.0002 | 0.3 |
| 10 | N,N-Bis(3-aminopropyl)-methylamine (100%) | 0.0003 | 0.5 |
| 11 | Jeffcat ZR-40 (99.1%) | 0.0030 | 5.0 |

[a]comparative data, not according to the invention. As dicamba dimethylamine salt the commercial Banvel ® was used. As dicamba 2-(-Aminoethoxy)ethanol salt the commercial Clarity ® was used.

TABLE 4

2,4-D salts

| Entry | Type of polyamine cation | Volatility (wt % loss per min) | Volatility (normed) |
| --- | --- | --- | --- |
| 1 | Dimethylamine[a] | 0.006 | 100.0 |
| 2 | Aminoethylethanolamine (99.9%) | 0.002 | 35.7 |

TABLE 4-continued 2,4-D salts

| Entry | Type of polyamine cation | Volatility (wt % loss per min) | Volatility (normed) |
|---|---|---|---|
| 3 | Jeffcat ® Z-130 (99.5%) | 0.0008 | 14.8 |
| 4 | Diethylenetriamine (98%) | 0.0008 | 13.7 |
| 5 | Tetraethylenepentamine (98%) | 0.0007 | 13.3 |

[a]comparative data, not according to the invention.

Example 3

Volatility of Dicamba Determined in Open Petri Dish

A dicamba sample of the aqueous solutions of dicamba (480 g/l) as prepared in Example 1 (Table 1, entry 2) was diluted with distilled water in a ratio of 1:50. To help spreading of the samples uniformly on the surface of the plate, Silwet L-77 was added (0.1 wt %). A total of 300 μl of this diluted sample was applied per Petri dish (diameter 5 cm). The dishes were kept at an environment chamber (Barnstead Environ-Cab Lab-line 680A) with forced air flow (air vent out) up to one month at 50° C. and 30% humidity. Afterwards the plates were extracted with acetic acid/methanol and the pesticide quantified by HPLC (Columbus C18 column) to determine the volatile loss of dicamba acid. Thus it was demonstrated, that the aminoethylethanolamine salt of dicamba had a reduced volatility compared to commercial dicamba salt formulations.

TABLE 5

Petri dish volatility of Dicamba salts

| Entry | Type of polyamine cation | Volatility after 2 weeks (wt % loss) | Volatility after 4 weeks (wt % loss) |
|---|---|---|---|
| 1 | Dimethylamine[a] | 98.7 | 100 |
| 2 | 2-(-Aminoethoxy)ethanol[a] | 29.3 | 57.0 |
| 3 | Aminoethylethanolamine | 6.2 | 20.6 |

[a]comparative data, not according to the invention. As dicamba dimethylamine salt the commercial Banvel ® was used. As dicamba 2-(-aminoethoxy)ethanol salt the commercial Clarity ® was used.

Example 4

Volatility of Dicamba Determined in Bioassay

Soybeans were grown in a 3 inch (7.6 cm) pots for approximately 10 days until the first trifoliate is unfolded (not fully expanded). Using a track sprayer, eight glass Petri dishes (9 cm diameter) were treated with 4480 g active ingredient per ha (type of dicamba salt see Table 6). Immediately after treatment, eight Petri dishes and two soybean plants were placed in a tray (25×51 cm) and covered with a plastic dome (25×51×20 cm). The covered trays were placed in a greenhouse with temperature maintained at 25-35° C. and 50-80% humidity. After 24 h of exposure, the plastic dome was removed. The percentage of injury of soybean plants (epinasty and stunting; visually evaluated compared to untreated plants), which is an indication of dicamba volatility, was assessed 14 days later. The results are summarized in Table 6. The data were normalized to 30% injury for the dicamba salt of 2-(-aminoethoxy)ethanol, which is commercially available dicamba salt (e.g. Clarity®).

TABLE 6

Dicamba salts

| Entry | Type of polyamine cation | Injury (%) |
|---|---|---|
| 1 | — (Dicamba acid)[a] | 67 |
| 2 | Dimethylamine[a] | 48 |
| 3 | 2-(-Aminoethoxy)ethanol[a] | 30 |
| 4 | Isophorone diamine | 19 |
| 5 | Aminoethylethanolamine | 5 |
| 6 | Aminoethylpiperazine | 19 |
| 7 | Jeffcat ® Z-130 | 5 |
| 8 | Diethylenetriamine | 14 |
| 9 | Tetraethylenepentamine | 6 |
| 10 | N,N-Bis(3-aminopropyl)methylamine | 7 |

[a]comparative data, not according to the invention. As dicamba dimethylamine salt the commercial Banvel ® was used. As dicamba 2-(-aminoethoxy)ethanol salt the commercial Clarity ® was used. As dicamba acid the commercial Vision ® was used.

Example 5

Herbicidal Activity of Dicamba Salts

In order to demonstrate the herbicidal effectiveness of the new salts of this invention (Table 1, entries 1 to 8), a series of tests was performed in comparison with the use of commercial dicamba dimethylamine salt and 2-(-aminoethoxy)ethanol salt. In each instance the test materials were sprayed onto ivy leaf morning glory, common lambs quarters, and velvet leaf weeds by standard post-emergence herbicidal test procedures. The results showed that all new dicamba salts gave statistically the same weed control as commercial dicamba dimethylamine salt and 2-(-aminoethoxy)ethanol salt, showing that the various salts do not affect herbicidal activity.

Example 6

Preparation of Glyphosate Salts

Salts were prepared comprising glyphosate (480 g/l) as pesticide anion and various polyamine cations (Table 7) as described in Example 1. It was found, that all tested salts have a very good solubility in water, i.e. that glyphosate salts are soluble up to at least 480 g/l.

TABLE 7

Glyphosate salts

| Entry | Type of polyamine cation |
|---|---|
| 1 | Diethylenetriamine[a] |
| 2 | Isophorone diamine |
| 3 | Aminoethylpiperazine |
| 4 | N,N-Bis(3-aminopropyl)methylamine |

[a]comparative data, not according to the invention.

Example 7

Volatility Determined by TGA of Glyphosate Salts

The volatility of the aqueous solutions of glyphosate salts as prepared in Example 6 was determined by analyzing the wt % loss per minute as described in Example 3. The results of the volatility (as wt % loss per min) are summarized in Table 8. Thus it was demonstrated, that the polyamine salts of glyphosate according to the invention had a volatility comparable to the known glyphosate diethylenetriamine salt. However, the boiling points of the neutral polyamines (isophorone diamine, aminoethylpiperazine, N,N-bis(3-aminopropyl)methylamine) were higher compared to the neutral diethylenetriamine. This is an important advantage of the polyamine salts according to the invention, because in aqueous solution the polyamine anion is partly present as neutral polyamine. Thus, the increased boiling point of the neutral polyamine results also in a decreased volatility of the neutral polyamine.

TABLE 8

Glyphosate salts

| Entry | Type of polyamine cation | Volatility (wt % loss per min) | $B_p$ of polyamine[b] |
|---|---|---|---|
| 1 | Diethylenetriamine[a] | 0.002 | 207° C. |
| 2 | Isophorone diamine | 0.002 | 247° C.[c] |
| 3 | Aminoethylpiperazine | 0.002 | 222° C. |
| 4 | N,N-Bis(3-aminopropyl)-methylamine | 0.002 | 235° C. |

[a]comparative data, not according to the invention.
[b]Boiling point of the neutral polyamine at 1 bar.
[c]Boiling point at 6 mbar.

The invention claimed is:

1. A salt comprising an anionic pesticide A1, wherein all anionic groups of said anionic pesticide are selected from one or more carboxylate groups and wherein the anionic pesticide A1 is an aromatic acid herbicide or a phenoxycarboxylic acid herbicide;
and a cationic polyamine (B) of the formula (B1)

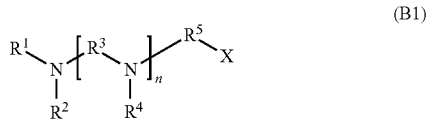

(B1)

wherein $R^1$, $R^2$, $R^4$, $R^6$, and $R^7$ are independently H or $C_1$-$C_6$-alkyl, which is optionally substituted with OH, $R^3$ and $R^5$ are independently $C_2$-$C_4$-alkylene, X is OH or $NR^6R^7$, and n is from 1 to 20;
or of the formula (B2)

(B2)

wherein $R^{10}$ and $R^{11}$ are independently H or $C_1$-$C_6$-alkyl, $R^{12}$ is $C_1$-$C_{12}$-alkylene, and
$R^{13}$ is an aliphatic $C_5$-$C_8$ ring system, which either comprises nitrogen in the ring or is substituted with at least one unit $NR^{10}R^{11}$, and wherein (B2) is free of ether groups, and wherein the anionic pesticide is dicamba.

2. The salt according to claim 1, wherein $R^1$, $R^2$, $R^4$, $R^6$, and $R^7$ are independently H or methyl, $R^3$ and $R^5$ are independently $C_2$-$C_3$-alkylene, X is OH or $NR^6R^7$, and n is from 1 to 10.

3. The salt according to claim 1, wherein $R_{10}$ and $R_{11}$ are independently H or methyl, $R_{12}$ is $C_2$-$C_3$-alkylene, and $R_{13}$ is an aliphatic $C_5$-$C_8$ ring system, which comprises nitrogen in the ring.

4. An agrochemical composition comprising at least one salt according to claim 1.

5. A method of controlling undesired vegetation, which comprises allowing a herbicidal effective amount of the agrochemical composition according to claim 4 to act on plants, their habitat or on seed of said plants.

6. The agrochemical composition of claim 4, comprising 10-70 wt % of the salt;
30-90 wt % water;
optionally a further pesticide; and
optionally up to 10 wt % auxiliaries, wherein the amount of all components adds up to 100 wt %.

7. A method for preparing the salt according to claim 1 comprising combining
the pesticide in its neutral form or as salt, and
the polyamine in its neutral form or as salt.

8. The method according to claim 7, wherein the pesticide and the polyamine are combined in water.

9. A method of combating harmful insects and/or phytopathogenic fungi, which comprises contacting plants, seed, soil or habitat of plants in or on which the harmful insects and/or phytopathogenic fungi are growing or may grow, plants, seed or soil to be protected from attack or infestation by said harmful insects and/or phytopathogenic fungi with an effective amount of an agrochemical formulation comprising the salt of claim 1.

10. The method of claim 9, wherein $R^1$, $R^2$, $R^4$, $R^6$, and $R^7$ are independently H or methyl, $R^3$ and $R^5$ are independently $C_2$-$C_3$-alkylene, X is OH or $NR^6R^7$, and n is from 1 to 10.

11. The method of claim 9, wherein $R_{10}$ and $R_{11}$ are independently H or methyl, $R_{12}$ is $C_2$-$C_3$-alkylene, and $R_{13}$ is an aliphatic $C_5$-$C_8$ ring system, which comprises nitrogen in the ring.

12. Seed treated with the salt according to claim 1.

13. The salt according to claim 1, wherein the polyamine (B) has the formula B1.1 or B1.2:

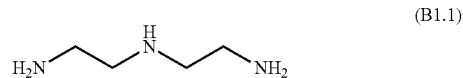

(B1.1)

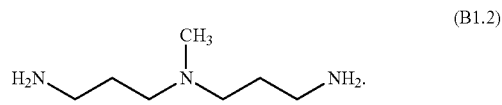

(B1.2)

14. The salt according to claim 1, wherein the ionic pesticide is dicamba and the cationic polyamine (B) has the formula B1.1:

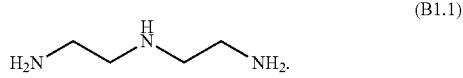

(B1.1)

15. The salt according to claim 1, wherein the ionic pesticide is dicamba and the cationic polyamine (B) has the formula B1.2:

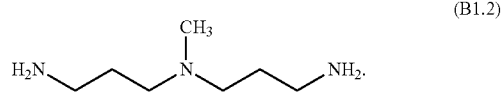

(B1.2)

* * * * *